(12) United States Patent
Tsang et al.

(10) Patent No.: US 11,980,532 B2
(45) Date of Patent: May 14, 2024

(54) DISPOSABLE ABSORBENT ARTICLE WITH PROFILED ABSORBENT CORE

(71) Applicant: DSG Technology Holdings Ltd., Kwai Chung (HK)

(72) Inventors: Patrick King Yu Tsang, Tuen Mun (HK); Anne Smid, Wolvega (NL); Andrew C. Wright, Rotherham (GB); Eugenio G. Varona, Marietta, GA (US)

(73) Assignee: DSG Technology Holdings Ltd., Kwai Chung (HK)

( * ) Notice: Subject to any disclaimer, the term of this patent is extended or adjusted under 35 U.S.C. 154(b) by 206 days.

(21) Appl. No.: 17/404,019

(22) Filed: Aug. 17, 2021

(65) Prior Publication Data

US 2022/0031525 A1 Feb. 3, 2022

Related U.S. Application Data

(63) Continuation of application No. 15/435,991, filed on Feb. 17, 2017, now Pat. No. 11,110,012, which is a
(Continued)

(51) Int. Cl.
*A61F 13/49* (2006.01)
*A61F 13/494* (2006.01)
(Continued)

(52) U.S. Cl.
CPC .. *A61F 13/49017* (2013.01); *A61F 13/49019* (2013.01); *A61F 13/49058* (2013.01);
(Continued)

(58) Field of Classification Search
CPC .......... A61F 13/49017; A61F 13/49019; A61F 2013/49025; A61F 2013/49033; A61F 2013/530861; A61F 2013/5355
See application file for complete search history.

(56) References Cited

U.S. PATENT DOCUMENTS 4,216,773 A  8/1980  Ryan
4,294,240 A * 10/1981 Thill ...................... A61L 15/12
602/21
(Continued)

FOREIGN PATENT DOCUMENTS

EP  0238334 A1  9/1987
EP  0321980 A2  6/1989
(Continued)

OTHER PUBLICATIONS

International Preliminary Report on Patentability dated Mar. 2, 2012 (issued in PCT Application No. PCT/US2010/002858) [32 pages].
(Continued)

*Primary Examiner* — Kathryn E Ditmer
(74) *Attorney, Agent, or Firm* — Alberto Q. Amatong, Jr.; Amatong McCoy LLC

(57) ABSTRACT

A disposable absorbent article has a central body defining a first waist end region including a first end edge, a second waist end region spaced longitudinally from the first waist end region and including a second end edge, and a crotch region positioned therebetween. An absorbent core is situated between the end edges, and includes a plurality of elastics incorporated therewith such that the core is substantially lat-erally contracted in a narrowed region about the elastics. The absorbent core includes at least one end region that is sub-stantially non-elasticized and has a lateral width substantially wider than that of the narrowed region.

28 Claims, 19 Drawing Sheets

Related U.S. Application Data continuation of application No. 14/163,763, filed on Jan. 24, 2014, now Pat. No. 9,603,754, which is a continuation of application No. 12/925,765, filed on Oct. 28, 2010, now Pat. No. 8,702,671.

(60) Provisional application No. 61/279,923, filed on Oct. 28, 2009.

(51) Int. Cl.
    *A61F 13/53*     (2006.01)
    *A61F 13/532*    (2006.01)
    *A61F 13/533*    (2006.01)
    *A61F 13/535*    (2006.01)
    *A61F 13/539*    (2006.01)

(52) U.S. Cl.
    CPC .... *A61F 13/49426* (2013.01); *A61F 13/5323* (2013.01); *A61F 13/533* (2013.01); *A61F 13/535* (2013.01); *A61F 13/539* (2013.01); *A61F 2013/530861* (2013.01); *A61F 2013/5355* (2013.01)

(56) References Cited

U.S. PATENT DOCUMENTS

| | | | |
|---|---|---|---|
| 4,323,070 A | 4/1982 | Ternstrom et al. | |
| 4,606,964 A | 8/1986 | Wideman | |
| 4,692,163 A | 9/1987 | Widlund et al. | |
| 4,760,764 A | 8/1988 | Jonckheere et al. | |
| 4,762,521 A | 8/1988 | Roessler et al. | |
| 4,775,375 A | 10/1988 | Aledo | |
| 4,886,511 A | 12/1989 | Korpman | |
| 4,891,258 A | 1/1990 | Fahrenkrug | |
| 4,897,084 A | 1/1990 | Ternstrom et al. | |
| 4,911,701 A | 3/1990 | Mavinkurve | |
| 5,295,987 A * | 3/1994 | Widlund | A61F 13/532 604/385.26 |
| 5,366,452 A * | 11/1994 | Widlund | A61F 13/15593 156/496 |
| 5,397,316 A * | 3/1995 | LaVon | A61F 13/5376 604/382 |
| 5,527,300 A | 6/1996 | Sauer | |
| 5,536,555 A * | 7/1996 | Zelazoski | B32B 3/266 428/152 |
| 5,562,793 A | 10/1996 | Menard | |
| 5,576,090 A | 11/1996 | Suzuki | |
| 5,597,437 A | 1/1997 | Lange et al. | |
| 5,662,634 A * | 9/1997 | Yamamoto | A61F 13/5323 604/378 |
| 5,681,302 A | 10/1997 | Melbye et al. | |
| 5,695,846 A | 12/1997 | Lange et al. | |
| 5,804,021 A * | 9/1998 | Abuto | B32B 27/40 428/152 |
| 5,868,724 A * | 2/1999 | Dierckes, Jr. | A61F 13/15707 604/375 |
| 5,906,602 A | 5/1999 | Weber et al. | |
| 6,090,090 A | 7/2000 | Roe et al. | |
| 6,222,092 B1 * | 4/2001 | Hansen | A61F 13/49406 604/385.101 |
| 6,258,196 B1 | 7/2001 | Suzuki et al. | |
| 6,262,331 B1 * | 7/2001 | Nakahata | A61F 13/531 604/383 |
| 6,437,214 B1 | 8/2002 | Everett et al. | |
| 6,520,945 B1 * | 2/2003 | Hansson | A61F 13/4702 604/385.24 |
| 6,561,354 B1 | 5/2003 | Fereshtehkhou et al. | |
| 6,569,137 B2 | 5/2003 | Suzuki et al. | |
| 6,610,039 B1 | 8/2003 | Wilhelm et al. | |
| 6,736,923 B1 | 5/2004 | Franzmann et al. | |
| 6,794,557 B1 | 9/2004 | Klemp et al. | |
| 6,840,929 B2 | 1/2005 | Kurata | |
| 6,913,718 B2 | 7/2005 | Ducker et al. | |
| 7,037,299 B2 | 5/2006 | Turi et al. | |
| 7,087,044 B2 | 8/2006 | Ohnishi | |
| 7,090,667 B2 | 8/2006 | Fell et al. | |
| 7,345,004 B2 | 3/2008 | Zenker et al. | |
| 7,780,643 B2 | 8/2010 | Persson | |
| 8,235,961 B2 | 8/2012 | Nakaoka et al. | |
| 2001/0014797 A1 | 8/2001 | Suzuki et al. | |
| 2001/0039700 A1 | 11/2001 | Krueger | |
| 2001/0047159 A1 | 11/2001 | Mizutani | |
| 2002/0082576 A1 * | 6/2002 | Hansson | A61F 13/47263 604/383 |
| 2002/0169428 A1 | 11/2002 | Fell et al. | |
| 2003/0083630 A1 | 5/2003 | Fell et al. | |
| 2003/0087056 A1 | 5/2003 | Ducker et al. | |
| 2004/0030313 A1 | 2/2004 | Watanabe et al. | |
| 2004/0033750 A1 | 2/2004 | Everett et al. | |
| 2004/0127871 A1 | 7/2004 | Odorzynski et al. | |
| 2004/0193128 A1 | 9/2004 | Klemp et al. | |
| 2004/0253892 A1 | 12/2004 | Baker et al. | |
| 2005/0015068 A1 | 1/2005 | Bean et al. | |
| 2005/0033254 A1 | 2/2005 | Fell et al. | |
| 2005/0055000 A1 * | 3/2005 | Ohnishi | A61F 13/49019 604/385.01 |
| 2005/0113791 A1 | 5/2005 | Neubauer et al. | |
| 2005/0137552 A1 | 6/2005 | Hansson et al. | |
| 2005/0143703 A1 | 6/2005 | Persson | |
| 2005/0148983 A1 * | 7/2005 | Doverbo | A61F 13/15699 604/385.101 |
| 2006/0047257 A1 | 3/2006 | Raidel et al. | |
| 2006/0184146 A1 | 8/2006 | Suzuki | |
| 2006/0206073 A1 | 9/2006 | Crane et al. | |
| 2007/0078424 A1 | 4/2007 | Wu et al. | |
| 2007/0093164 A1 * | 4/2007 | Nakaoka | A61F 13/536 442/385 |
| 2007/0135787 A1 | 6/2007 | Raidel et al. | |
| 2007/0148433 A1 | 6/2007 | Mallory et al. | |
| 2007/0233029 A1 | 10/2007 | Jansson et al. | |
| 2008/0063837 A1 * | 3/2008 | Pansy | A61F 13/4902 428/317.1 |
| 2009/0062760 A1 * | 3/2009 | Wright | A61F 13/15747 604/378 |
| 2010/0100022 A1 * | 4/2010 | Greener | A61F 13/00995 83/13 |
| 2011/0130736 A1 | 6/2011 | Tsang et al. | |
| 2013/0011601 A1 | 1/2013 | Fenske | |

FOREIGN PATENT DOCUMENTS

| | | | |
|---|---|---|---|
| EP | 0670153 A1 | 9/1995 | |
| EP | 0801551 A1 | 10/1997 | |
| EP | 0904755 A2 | 3/1999 | |
| EP | 0969786 A1 | 1/2000 | |
| EP | 1011579 A1 | 6/2000 | |
| EP | 1018981 A2 | 7/2000 | |
| EP | 1019002 A1 | 7/2000 | |
| EP | 1019003 A1 | 7/2000 | |
| EP | 1021152 A1 | 7/2000 | |
| EP | 1062929 A1 | 12/2000 | |
| EP | 1116479 A2 | 7/2001 | |
| EP | 1621168 A1 | 2/2006 | |
| GB | 2262873 A * | 7/1993 | ....... A61F 13/49019 |
| GB | 2310606 A * | 9/1997 | ........... A61F 13/512 |
| WO | 9534264 A1 | 12/1995 | |
| WO | 9621411 A1 | 7/1996 | |
| WO | 9825999 A1 | 6/1998 | |
| WO | 9843575 A1 | 10/1998 | |
| WO | 9908639 A1 | 2/1999 | |
| WO | 0071068 A1 | 11/2000 | |
| WO | 0100123 A1 | 1/2001 | |
| WO | 0105440 A2 | 1/2001 | |
| WO | 0245637 A1 | 6/2002 | |
| WO | 02092898 A1 | 11/2002 | |
| WO | 03039850 A1 | 5/2003 | |
| WO | 2004060227 A1 | 7/2004 | |
| WO | 2005004764 A1 | 1/2005 | |
| WO | 2005055895 A1 | 6/2005 | |
| WO | 2005060892 A1 | 7/2005 | |
| WO | 2005063160 A1 | 7/2005 | |

(56) References Cited

FOREIGN PATENT DOCUMENTS

| WO | 2006025934 A1 | 3/2006 |
| WO | 2006059922 A1 | 6/2006 |
| WO | 2007069966 A1 | 6/2007 |
| WO | 2007070183 A2 | 6/2007 |
| WO | 2009008788 A1 | 1/2009 |

OTHER PUBLICATIONS

International Search Report and Written Opinion dated Jan. 10, 2011 (issued in PCT Application No. PCT/US2010/002858) [13 pages].
Supplementary European Search Report dated Oct. 22, 2013 (issued in EP Application No. 10828653.5) [9 pages].

* cited by examiner

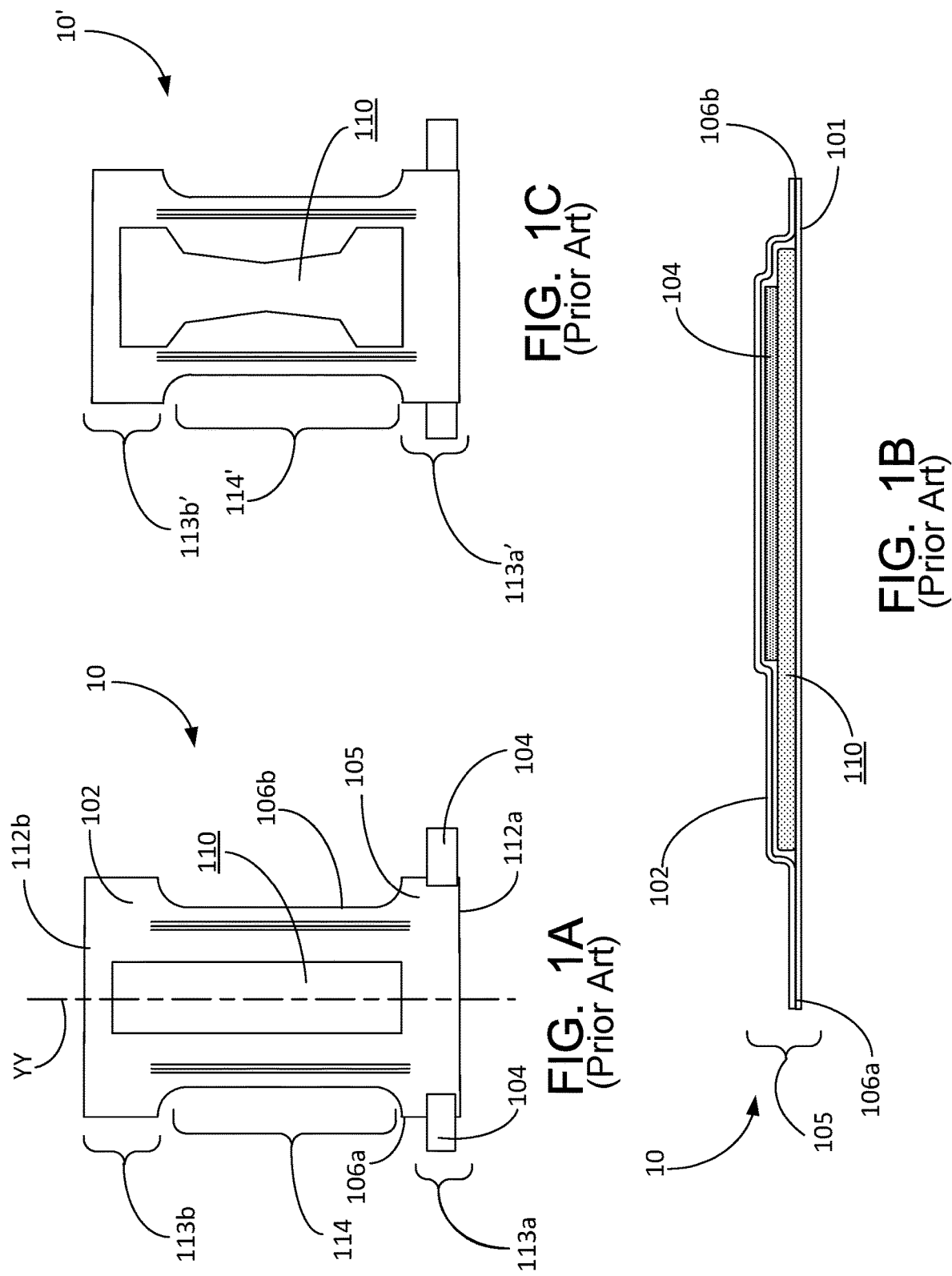

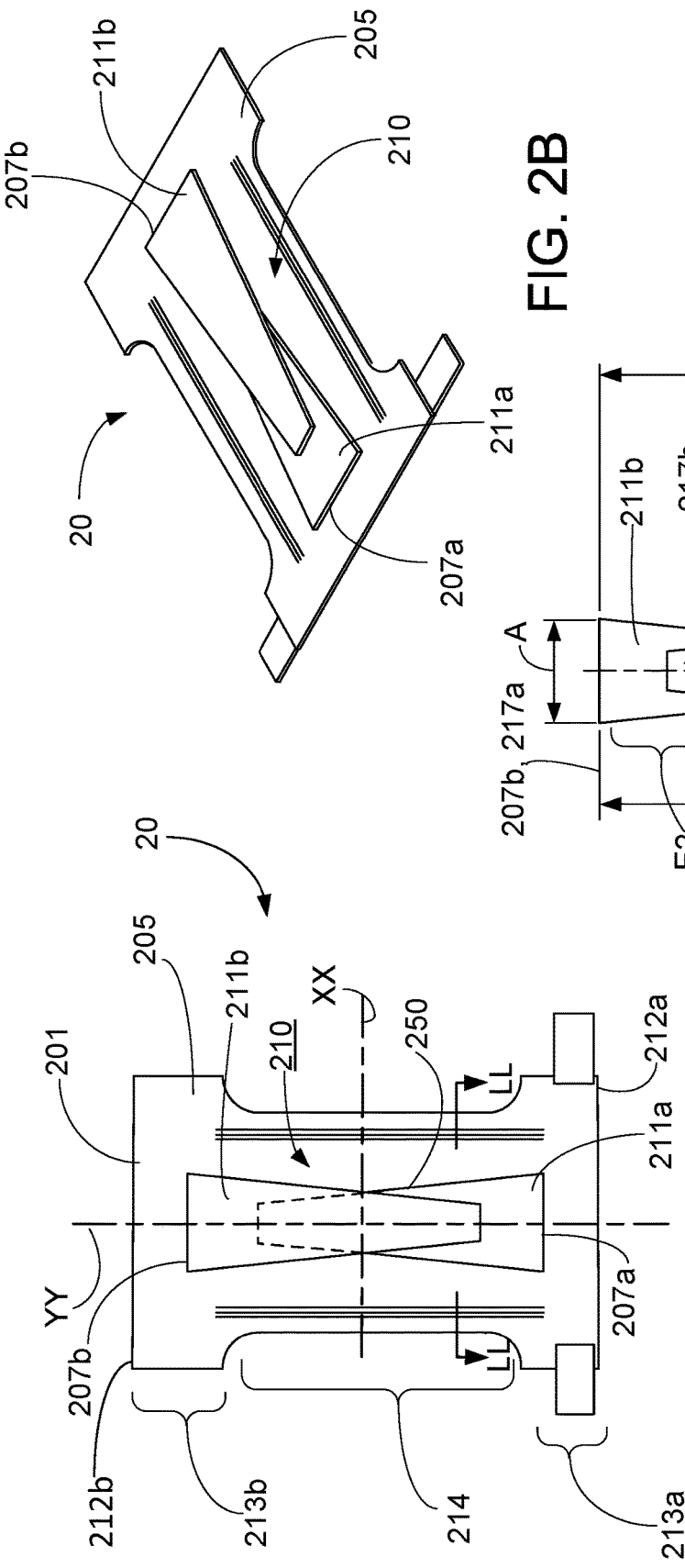
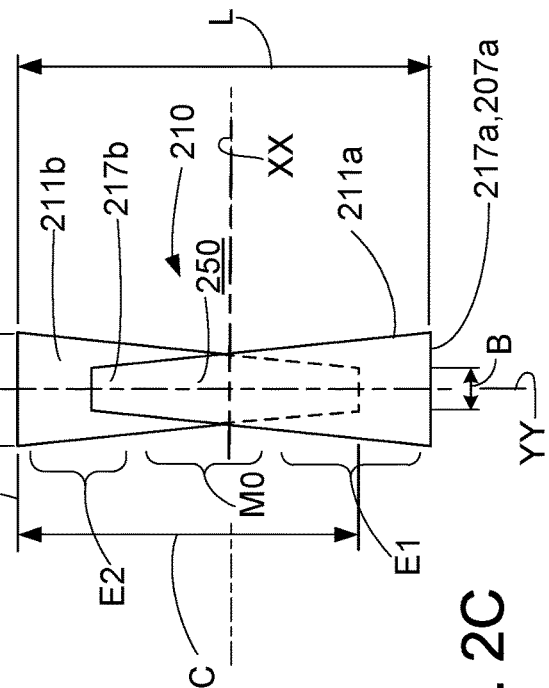
FIG. 2A
FIG. 2B
FIG. 2C

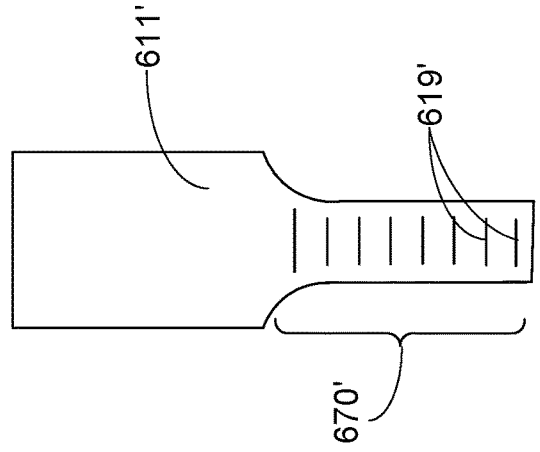
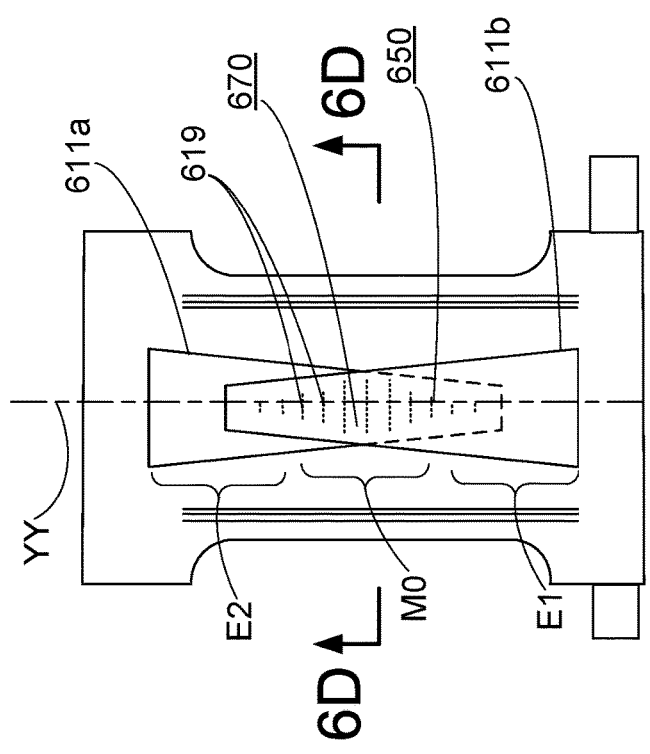
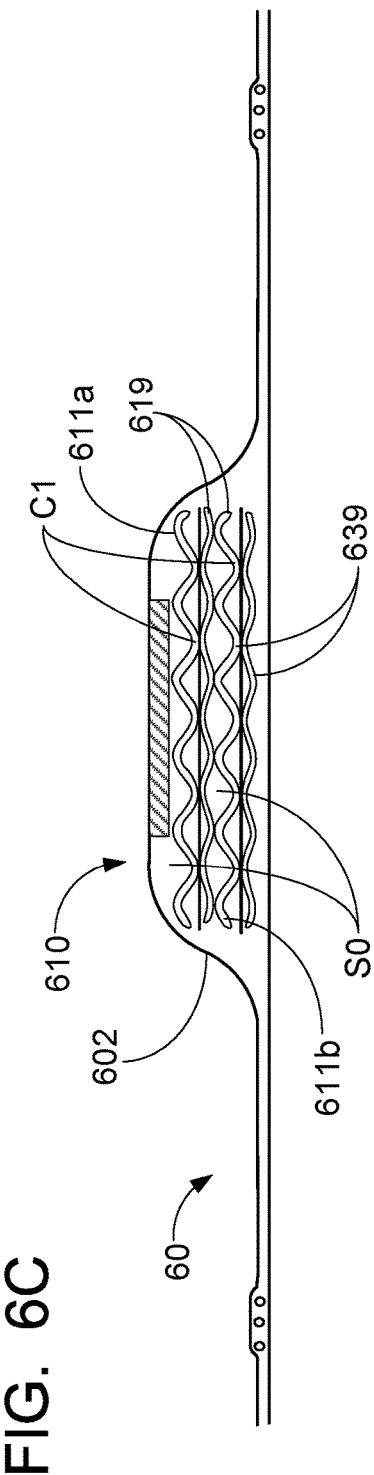
FIG. 6C
FIG. 6E
FIG. 6D

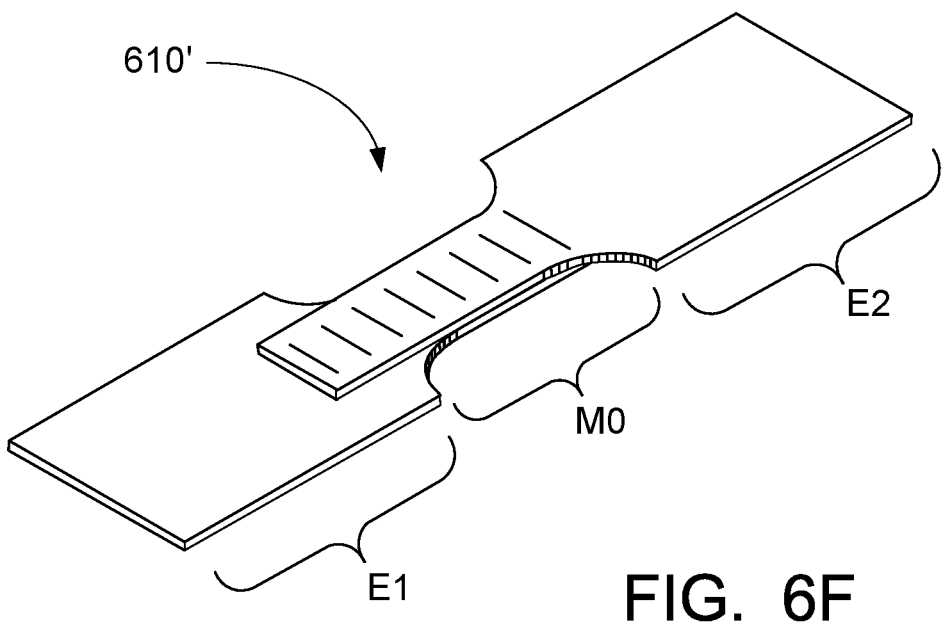
FIG. 6F
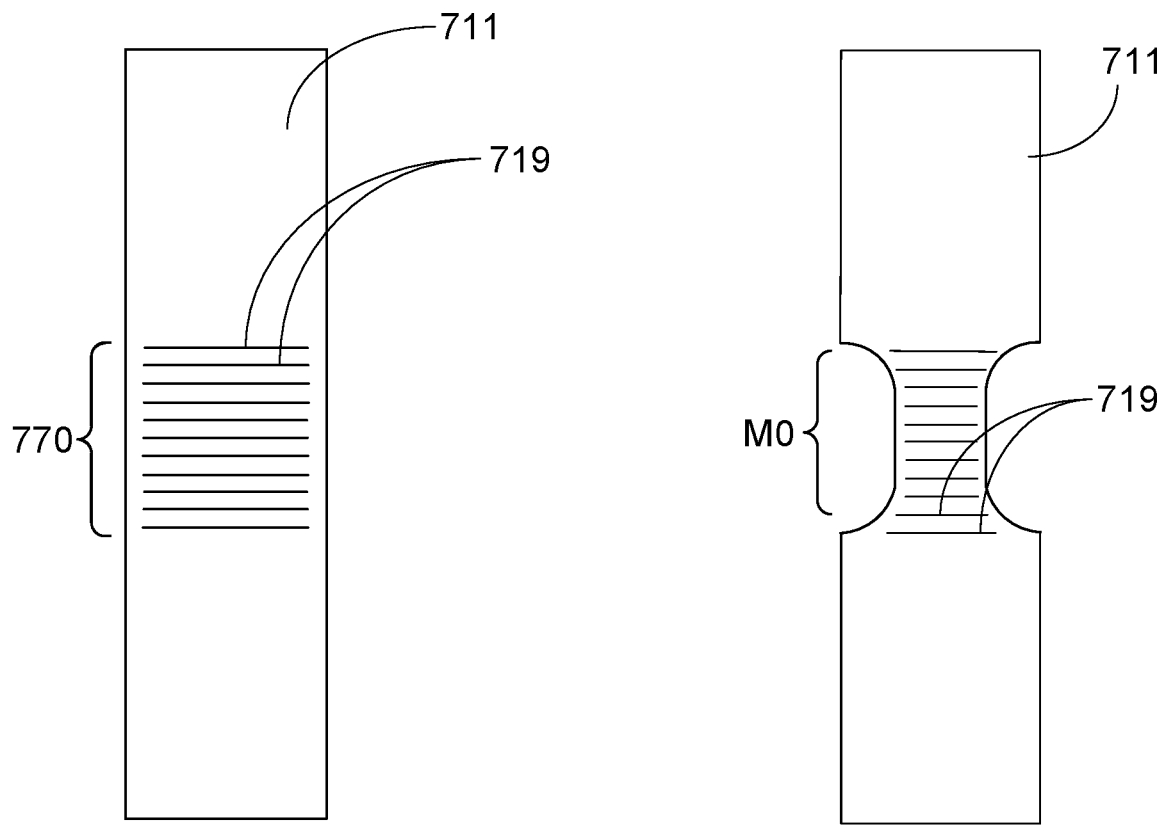
FIG. 7A
FIG. 7B

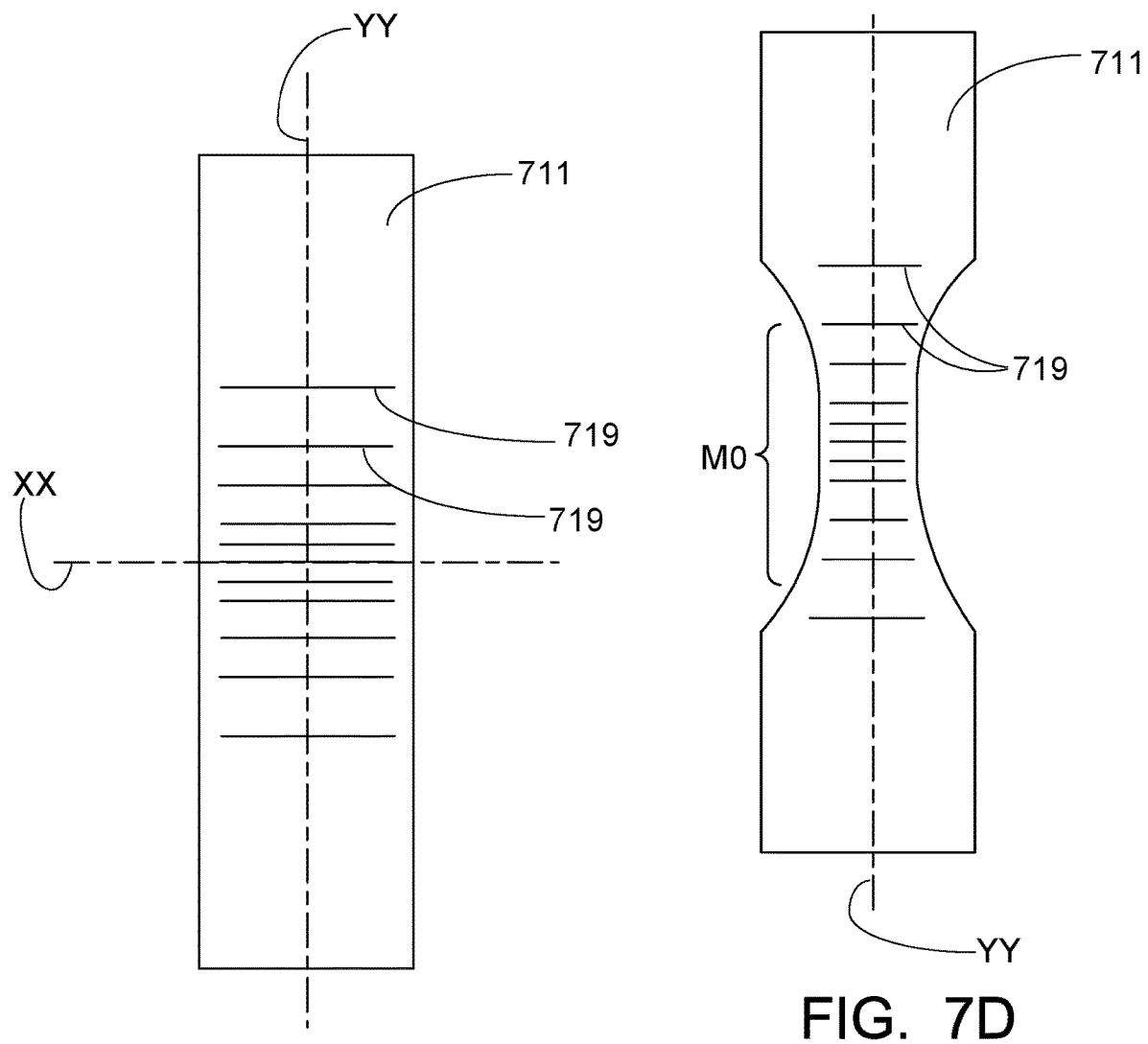
FIG. 7C
FIG. 7D
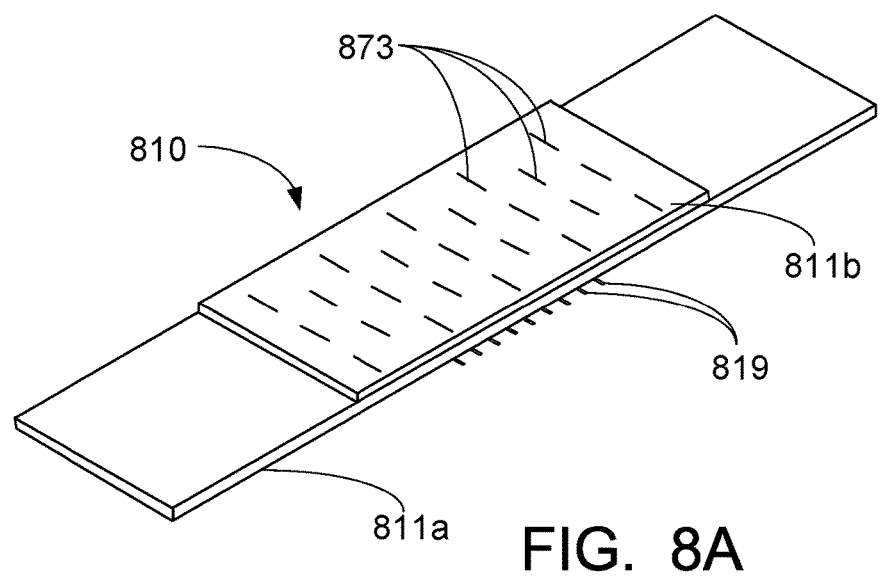
FIG. 8A

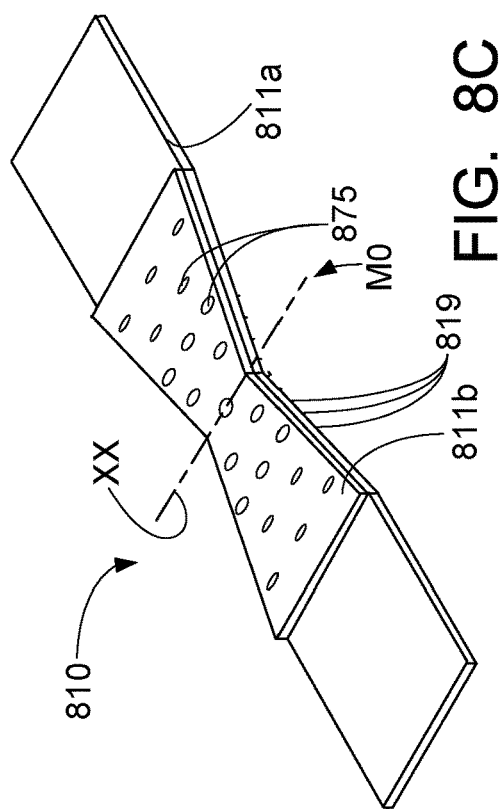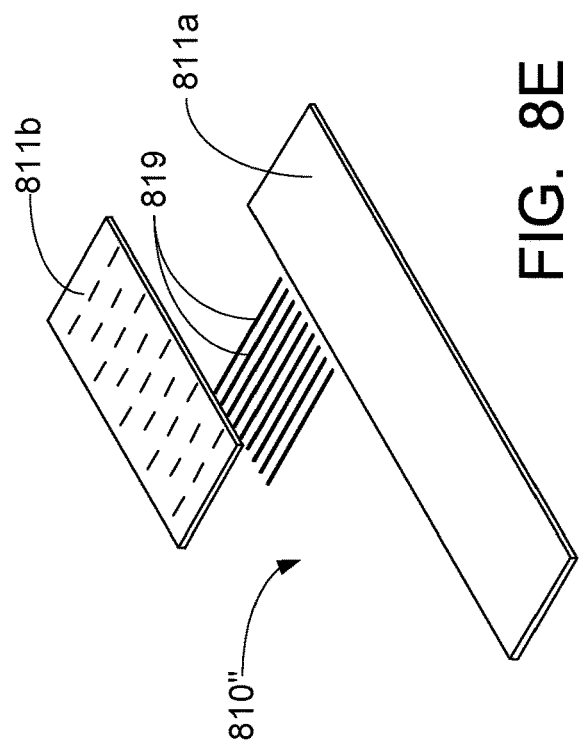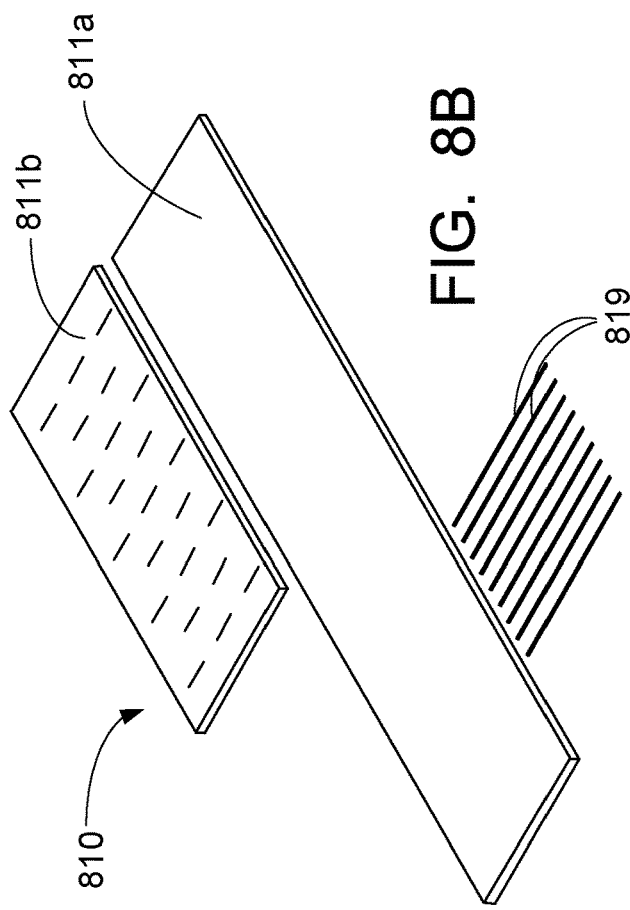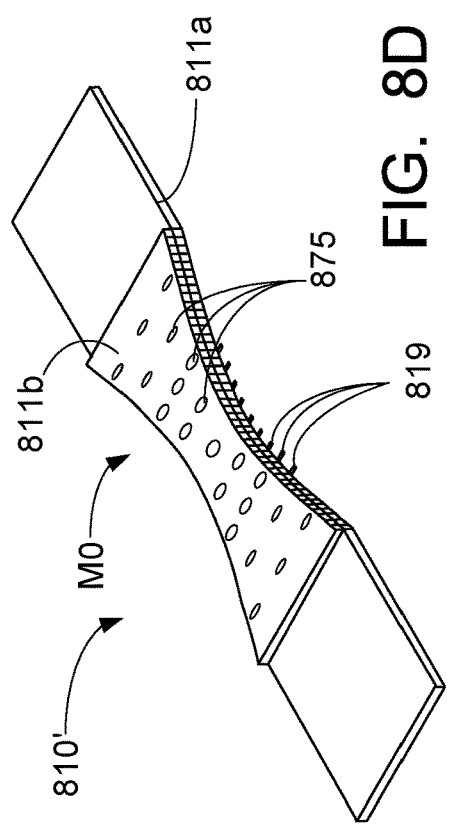

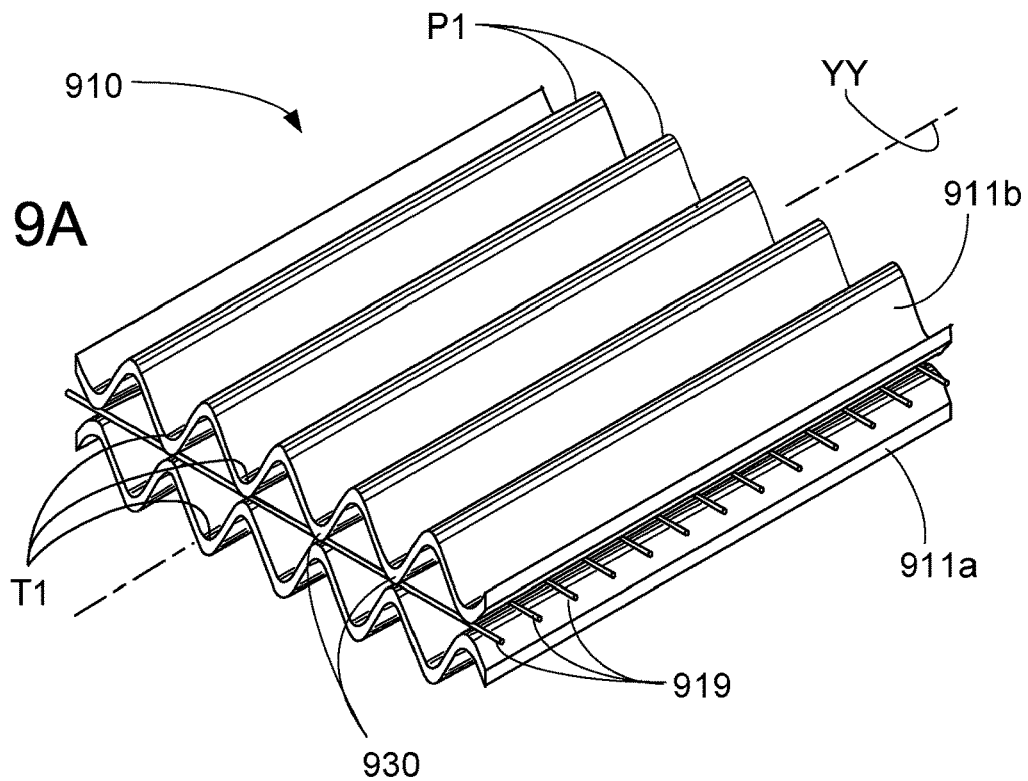
FIG. 9A
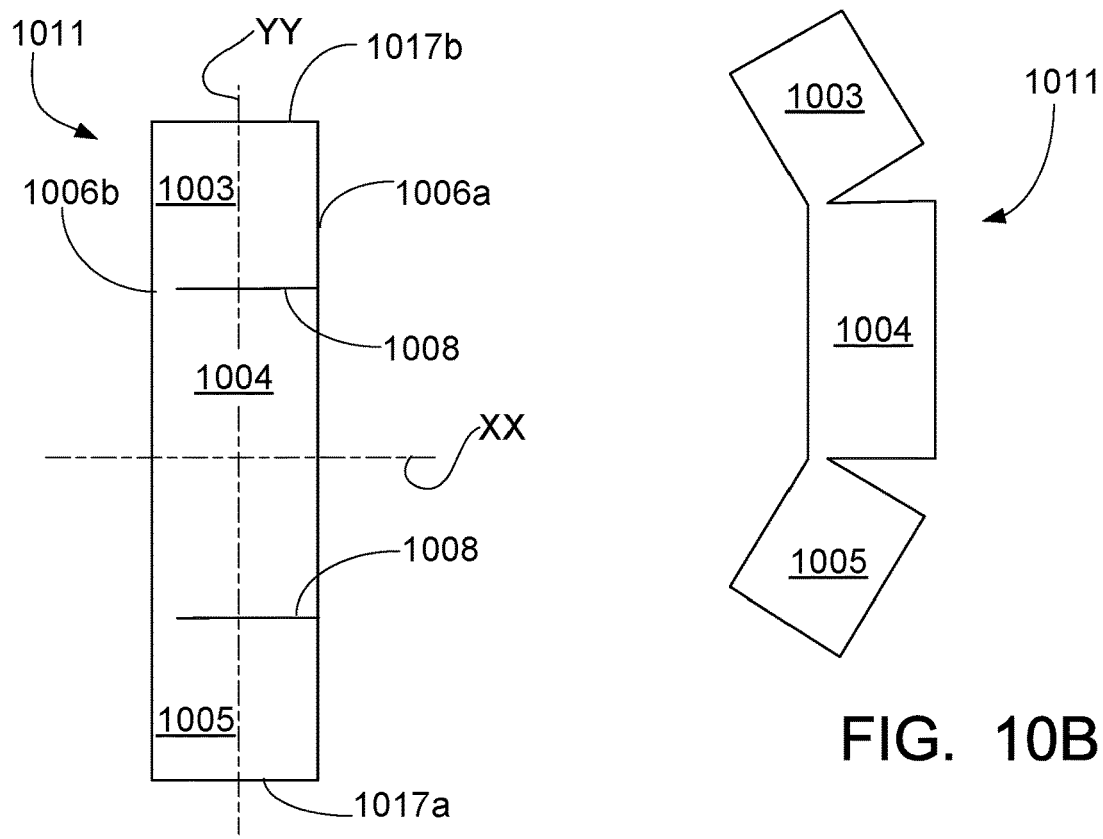
FIG. 10A
FIG. 10B

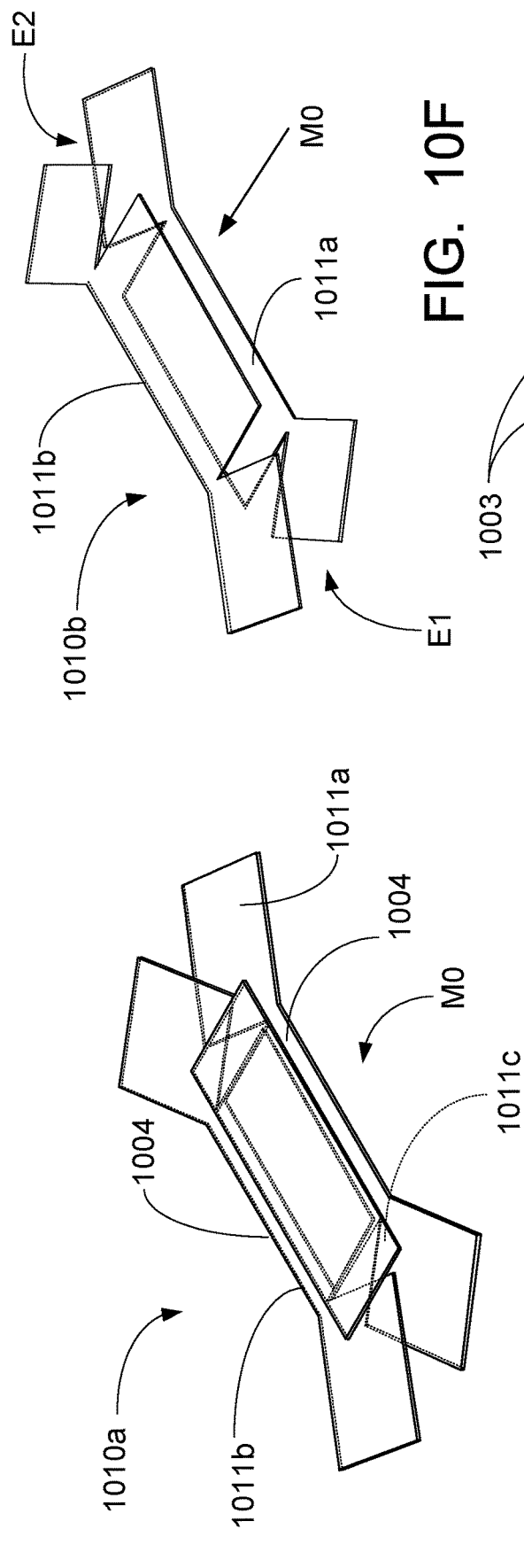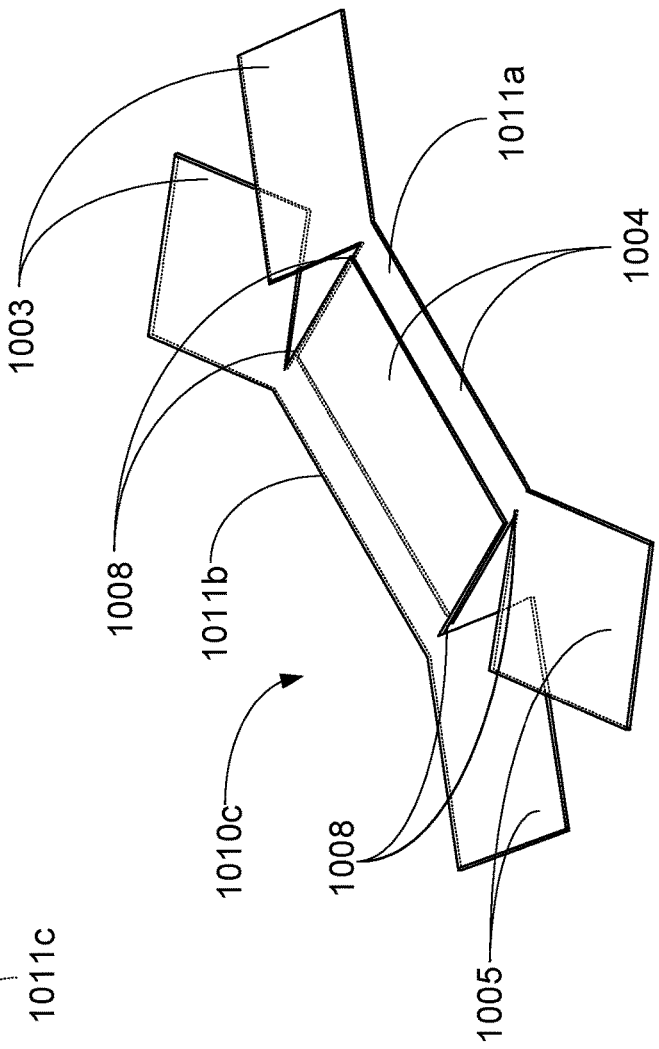
FIG. 10F
FIG. 10D
FIG. 10G

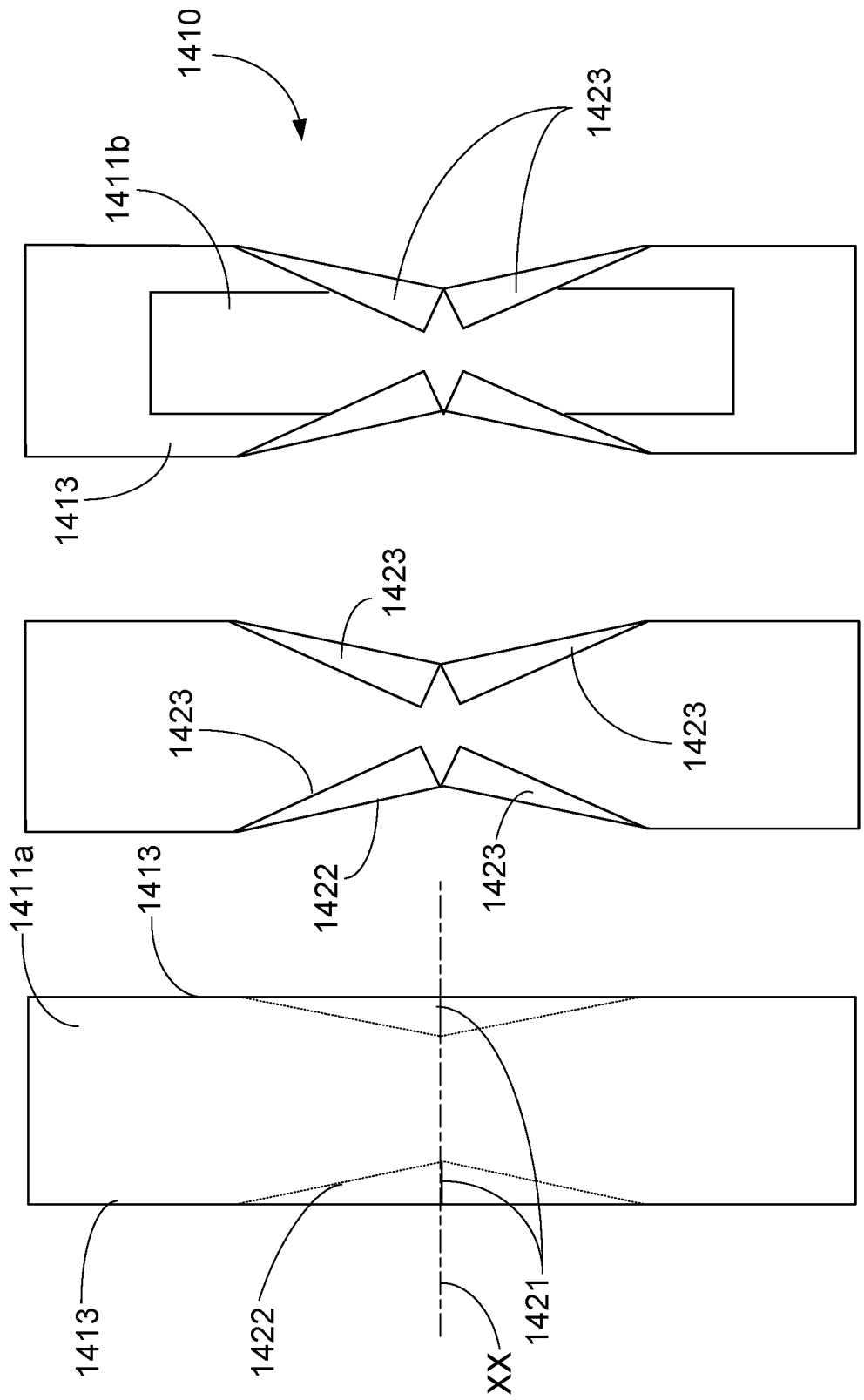

US 11,980,532 B2

DISPOSABLE ABSORBENT ARTICLE WITH PROFILED ABSORBENT CORE

CROSS-REFERENCE TO RELATED APPLICATIONS

The present application is a Continuation of U.S. patent application Ser. No. 15/435,991, filed Feb. 17, 2017 (now allowed), which is a Continuation of U.S. application Ser. No. 14/163,763, filed Jan. 24, 2014 (now U.S. Pat. No. 9,603,754), which is a Continuation of U.S. application Ser. No. 12/925,765, filed Oct. 28, 2010 (now U.S. Pat. No. 8,702,671), which claims the benefit of the filing date of U.S. Provisional Application Ser. No. 61/279,923 filed on Oct. 28, 2009, which are hereby incorporated by reference for all purposes and made a part of the present disclosure.

BACKGROUND OF THE INVENTION

The present invention relates generally to disposable absorbent articles, such as baby diapers, training pants, adult incontinence products, feminine hygiene articles, and the like. More particularly, the present invention relates to improved absorbent core components, disposable absorbent articles utilizing such absorbent core components, and a method of making or manufacturing same.

An advantageous application of the various concepts and embodiments of the present invention is one directed to baby diapers. For this reason, much of the exemplary descriptions provided herein are directed to diapers. The invention extends, of course, to applications beyond diapers.

Most absorbent articles used today as baby diapers have a configuration similar to the absorbent article 10 depicted in FIGS. 1A and 1B. The conventional absorbent article 10 is shown in a laid out flat position in FIG. 1A, and in cross sectional view in FIG. 1B. This absorbent article 10 includes an outer-side fluid impermeable backsheet 101, a bodyside, fluid permeable nonwoven coverstock or topsheet 102, and an absorbent construction 110 positioned between the backsheet 101 and topsheet 102. An absorbent core 103 provides the primary component of the absorbent construction 110 and is designed and positioned to receive and retain bodily fluids. The absorbent construction 110 may also include at least one fluid management, fluid distribution and/or surge layer 104.

As shown in FIG. 1A, the backsheet 101 and topsheet 102 together form or define a chassis or central body 105 of the absorbent article 10. The central body 105 may be described as having a first longitudinal end edge 112a, a second longitudinal end edge 112b, and a longitudinal centerline YY that extends through the central body 111, bisecting both the first and second end edges 112a, 112b. Left and side margins 106a, 106b extend from one end edge 112a to the other end edge 112b. Each end edge 112a, 112b partly defines waist regions 113a, 113b of the central body 105 which are generally characterized as having a lateral width significantly greater than a lateral width of a central region or crotch region 114 of the central body 105. The waist regions 113a, 113b are designed to allow the absorbent article 10 to be placed about the waist of the user. In this respect, the first and second waist regions 113a, 113b may be described as front and rear waist regions 113a, 113b, respectively. The conventional absorbent article 10 further includes a fastening means 104 attached to each side of the rear waist region 113a. The fastening means 104 are extendible and thereby, fastenable to a corresponding side of the front waist region 113b. The fastening means 104 helps to retain the article 10 around and on the body of the user. The absorbent article 10 also includes a means for elasticizing 107 the article 10 to maintain closure and sealing around the user's legs. The elasticizing means 1057 (e.g., leg cuffs and/or leg cutters) are necessarily positioned outboard of and along longitudinal side margins 106 of the absorbent construction 110. Referring to FIG. 1A, the conventional absorbent core 110 is centrally positioned in and about the crotch region 114 of the absorbent article 10.

Currently, most diaper cores are made from mixtures of fibers and superabsorbent particles, specifically cellulose based fibers derived from wood pulp and superabsorbent particles (SAP) derived from polyacrylic acid derivatives. An absorbent composite that is particularly suited for application in or with the disposable absorbent articles introduced herein is described in U.S. Pat. No. 6,540,853. SAP-non-woven absorbent composites of the type disclosed in this patent reference are available to the diaper manufacturing process in roll form and allow much greater freedom for the design of absorbent cores. Nevertheless, because fluff pulp-superabsorbent cores are generally provided as a continuous stream or web of absorbent material, the simpler and most cost efficient processes require the absorbent core to be maintained in a generally rectangular shape.

These cores are typically formed into rectangular shapes that are designed for incorporation into an absorbent article. The core shape, particularly its width, is maintained at dimensions that accommodate placement within a diaper corresponding with the crotch area of the user. Moreover, it is preferred in many applications for the absorbent core to take on a nearly hourglass shape. Such diaper cores are known in the art as providing a narrower crotch region that presents a better fit and comfort for the user. The hourglass shape also provides wider regions at the longitudinal ends of the core, which enhances the absorbency and leakage control capability of the diaper at those regions above the central crotch region.

FIG. 1C illustrates another prior art disposable absorbent article 10'. The absorbent article 10' employs a design in which an absorbent core 110' is reduced in width in the crotch region 114', but is wider at the front and rear waist regions 113a', 113b'. The result is an absorbent core 110' having a more hourglass shape. To achieve this desired hourglass shaped core, a rectangular absorbent core section is cut from a continuous web of absorbent material and shaped further, particularly in forming the narrow central region.

As known in the art, the preferred diaper assembly process is a substantially linear and efficient machine directed process that produces a high volume of packaged products. Because of the nature of the consumer product as a disposable, high frequency of use item and the abundance of competing products and alternative products (e.g., reusable cloth diapers), it is imperative to maintain the low cost of the final product. Accordingly, it is also imperative to control the complexity of the manufacturing process and to minimize steps and material waste. This presents a technical challenge to one attempting to create alternative shapes and functionalities in the conventional disposable absorbent article. For example, although an hourglass shaped diaper core is generally desirable or, in some applications, a core having distinct areas of absorbency, additional cutting or forming steps or increased material cost may make the alternative design less effective.

In any event, absorbent core configurations achieving further functionalities and/or improved fit and comfort for the sure are desirable. Caution must be exercised, however, to minimize material cost and manufacturing complexity.

SUMMARY OF THE INVENTION

The present invention is particularly directed to achieving absorbent core configurations that easily accommodate the conventional disposable absorbent article and maintains comfort and fit for the user. Such absorbent core configurations, and disposable absorbent articles employing same, are readily made at high volume without overburdening the manufacturing process with additional steps and material waste. In this respect, the invention provides improved hourglass or nearly hourglass shaped core constructions by providing and presenting more usable and flexible core components or core elements and incorporating these components into highly effective diapers, training pants and the like.

In one aspect, a disposable absorbent article is provided having a central body defining a first waist end region including a first longitudinal end edge, a second waist end region spaced longitudinally from the first waist end region and including a second longitudinal end edge, and a crotch region positioned therebetween. An absorbent core is situated between the end edges, and includes a first core element formed by materials imparting absorbent properties and a second core element formed by materials imparting absorbent properties. The second core element partially superimposes the first core element to form a multi-layer primary absorbent region of the absorbent core.

In another aspect, a disposable absorbent article is provided having a central body defining a first waist end region including a first end edge, a second waist end region spaced longitudinally from the first waist end region and including a second end edge, and a crotch region positioned therebetween. The absorbent core is situated between the end edges, and includes a plurality of elastics incorporated therewith such that the core is substantially laterally contracted in a narrowed region about the elastics. The absorbent core includes at least one end region that is substantially non-elasticized, and the at least one end region has a lateral width substantially wider than a lateral width of the narrowed region.

These exemplary aspects and other aspects of the invention are illustrated through FIGS. 1-14 and/or the Detailed Description provided below.

BRIEF DESCRIPTION OF THE DRAWINGS

FIG. 1A is a simplified plan view illustration of a prior art disposable absorbent article having an absorbent core;

FIG. 1B is a simplified cross-sectional view illustration of a prior art disposable absorbent article of the type depicted in FIG. 1A;

FIG. 1C is simplified plan view illustration of another prior art disposable absorbent article;

FIG. 2A is a simplified plan view illustration of a disposable absorbent article, with a partial cut-out revealing an absorbent core, according to the present invention;

FIG. 2B is a perspective view illustration of the disposable absorbent article in FIG. 2A;

FIG. 2C is an isolated plan view of the absorbent core in the disposable absorbent article in FIG. 2A;

FIG. 6C is a simplified plan illustration of a disposable absorbent article, including a pair of the absorbent cores in FIG. 6A, according to the present invention;

FIG. 6D is a simplified cross-sectional view of the disposable absorbent article in FIG. 6C across line 6D-6D;

FIG. 6E is a simplified plan illustration of one variation of the absorbent core in FIG. 6A;

FIG. 6F is an isolated perspective view of an absorbent core utilizing a pair of the absorbent core elements in FIG. 6E;

FIG. 7A is a simplified plan illustration of an alternate absorbent core according to the present invention, shown in a tensioned state;

FIG. 7B is a further illustration of the absorbent core in FIG. 7A in a relaxed or contracted state;

FIG. 7C is a simplified illustration of a variation of the absorbent core in FIG. 7A, in a tensioned state, according to the present invention;

FIG. 7D is an illustration of the absorbent core in FIG. 7C in a relaxed or contracted state;

FIG. 8A is a simplified perspective view of an elasticated absorbent core, shown in a tensioned state, according to the present invention;

FIG. 8B is an exploded view of the absorbent core in FIG. 8A;

FIG. 8C is a simplified, perspective view illustration of the absorbent core in FIG. 8A, shown in a relaxed or contracted state, according to the present invention;

FIG. 8D is a simplified, perspective view of an alternative elasticated absorbent core, according to the present invention;

FIG. 8E is an exploded view of yet another variation of an elasticated absorbent core, according to the present invention;

FIG. 9A is a perspective illustration of an elasticated absorbent core, according to yet another embodiment of the present invention;

FIG. 10A is a simplified illustration of an absorbent core element according to yet another embodiment of the present invention;

FIG. 10B is a further illustration of the absorbent core element in FIG. 10A, shown in an applied state;

FIG. 10D is a perspective view of an alternate absorbent core utilizing the absorbent core elements in FIG. 10A;

FIG. 10F is a simplified plan perspective illustration of an absorbent core utilizing the core elements in FIG. 10E;

FIG. 10G is a simplified plan illustration of yet another alternate absorbent core, according to the present invention;

FIG. 14A is a simplified plan illustration of an absorbent core element according to yet another embodiment of the present invention;

FIG. 14B is a plan illustration of the absorbent core element of FIG. 14A in a post-folding stage;

FIG. 14C is a simplified plan illustration of an alternative resultant absorbent core according to the present invention;

DETAILED DESCRIPTION OF PREFERRED EMBODIMENTS OF THE INVENTION

Figure 2D:
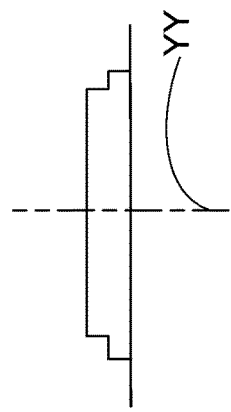
FIG. 2D is a cross sectional view illustrating a longitudinal absorbent profile of the absorbent article in FIG. 2A.

The present invention is directed, in one respect, to developing and utilizing alternate absorbent core designs that maintain or improve the comfort and fit of the absorbent article while also maintaining or improving the absorbency and sealing capability of the core and the absorbent article. Various embodiments of the invention place particular emphasis on selective placement and shaping of commercially available absorbent materials, while maintaining the cost efficiency and manufacturability of the resultant disposable absorbent article. In one aspect, emphasis is directed to selective placement and varying of absorbent materials along the longitudinal and/or lateral direction (i.e., absorbent profile) to achieve a certain functionality and efficiency. Selected absorbent profiles provide regions or expanse within the resultant core construction exhibiting advantageous or optimal absorbent or absorption capacity per unit area (sometimes referred to herein as "absorbent density" or "absorption density"). As mentioned briefly above, various aspects of the invention are particularly applicable to baby diapers (and also, training pants). For this reason, much of the description and illustrations herein are provided in the context of diapers. It will become apparent to one skilled in the art provided with the present disclosure, however, that the invention, and its various aspects, are also applicable to other disposable absorbent articles and absorbent core constructions. The detailed descriptions and illustrations of inventive embodiments should not, therefore, be construed as limiting the invention.

FIGS. 2A and 2B depict a disposable absorbent article 20, in the form of a diaper, embodying various aspects of the present invention, including an improved absorbent core construction 210 (see also FIG. 2C). The absorbent article 20 has a backsheet 201 and a topsheet 202 that is shown partially removed in FIG. 2A to reveal the absorbent core construction 210. Together, the combination of the backsheet 201 and topsheet 202 helps to define a chassis or central body 205 of the absorbent article 20. The central body 205 also provides a first waist end region 213a, including a first longitudinal end edge 212a (or simply, first end edge 212a), a second waist end region 213b, including a second longitudinal end edge 212b (or second end edge), and a longitudinal centerline YY extending the length of the central body 205 to bisect the first and second end edges 212a, 212b. Referring to FIG. 2A, the waist regions 213a, 213b may be identified with the portions of the absorbent article 20 and the central body 205 that are generally positioned vertically, and above and about the thighs of the user when the absorbent article 20 is worn.

The central body 205 also helps define a crotch region 214 located generally centrally between the first and second waist regions 213a, 213b and about a lateral centerline XX. As is readily known to consumers and manufacturers alike, much of the crotch region 214 is positioned generally horizontally and/or is curved upwards when the article 210 is in use. The absorbent core construction 210 is preferably centered and supported about the crotch region 214 between the backsheet 201 and topsheet 202. In such an arrangement, the absorbent construction 210 is placed in a nearly optimal position to receive bodily exudates when the absorbent article 20 is in use. The absorbent construction 210 is also described herein as having a first longitudinal end 207a (or simply, first end 207a) and a second longitudinal end 207b (or second end 207b) spaced longitudinally from the first end 212a and second end 212b of the central body 205, respectively. In some embodiments, the first and second ends 207a, 207b of the absorbent construction 210 may not be clearly defined, e.g., as an edge, line, or point. In such embodiments, the terms first and second ends are used to identify generally the margins of the absorbent construction or absorbent core spaced furthest along the longitudinal direction from the lateral centerline XX. In other embodiments, the first and second ends may not be defined by one core component or element, but by multiple components or elements.

To facilitate description and illustration, the absorbent core construction 210 is often illustrated and described as consisting only of layers of absorbent materials, as illustrated in FIGS. 2A-2C. The absorbent construction 210 is, therefore, simply referred to herein as an absorbent core 210. As will also become apparent with the descriptions of various embodiment of the invention, the absorbent core 210 may be composed of more than one independently applied core component or absorbent core element having significantly enhanced absorbent properties. In the embodiment of FIGS. 2A-2C, for example, the absorbent core 210 includes a first absorbent core element 211a and a second absorbent core element 211b that are applied separately during assembly. The absorbent core elements 211a, 211b may be constructed from any combination of nonwoven material, absorbent fibers and/or superabsorbent particles, as briefly discussed above. In this embodiment, the form of the absorbent core element 211a, 211b deviates from the conventional rectangular shape and takes on an irregular, non-rectangular shape that Applicants have discovered provides certain benefits or helps to achieve specific core functionalities and shapes.

As shown further in FIGS. 2B and 2C, the first and second absorbent core elements 211a, 211b are preferably provided in a generally trapezoidal shape. Among other things, the irregular shape of the core element 211 is conducive to forming an hourglass shaped absorbent core. In this embodiment, the first and second trapezoidal core elements 211a, 211b are preferably made of the same or substantially similar absorbent materials and, more preferably, originate from the same source or web of absorbent core composite to facilitate and ease manufacturing. In one aspect of the invention, the absorbent core elements 211a, 211b are also of the same shape, and thus, one core element may be substantially indistinguishable from another except for the position or orientation taken by the core element in the final assembly of the resultant absorbent core. This commonality and consistency facilitates manufacturing and. ultimately, helps to control product cost. For convenience, the core elements 211a, 211b may be referred to simply using the same reference numeral (i.e., 211). It should be noted, however, that other applications and further embodiments may require absorbent core elements having different properties or characteristics (e.g., absorbent properties) so as to achieve a particular overall absorbent core design or capability. The absorbent core elements may also take on very different shapes and configurations, as will be illustrated in other embodiments described in this Detailed Description.

The trapezoid shaped core elements 211 may be formed and applied by any number of suitable means including vacuum forming techniques, cutting with the aid of rotary dies, and cutting using waterjet devices. Referring to the top core element 211a in FIG. 2C, the width of each trapezoidal shaped absorbent core element 211 is tapered from a wide first end 217a or wide section to a narrow second end 217b or narrow section. As applied on the absorbent article 20, each trapezoidal shaped absorbent core element 211 is preferably positioned in alignment (co-incident) with the longitudinal centerline YY of the absorbent article 20 with the wide end 217a located proximate one of the waist regions 213 of the central body 205 and the narrow end 217b located more inwardly. The two core elements 211 are partially, mutually overlaid or superimposed near the center of the crotch region 214 such that the overlaid narrower sections form a dual layered section 250 (distinguished through use of cross-hatching in FIG. 2C) of the absorbent core 210. Moreover, the two core elements 211 are positioned as substantially mirror images of one another such that the resultant absorbent core 210 is generally symmetric about the longitudinal centerline YY and about the lateral centerline XX. In this configuration, the wider ends 217a of the core elements 211 provide, or coincide with, the longitudinal ends 217 of the resultant absorbent core 210.

It should be noted that because the two core elements 211 are identical in shape and in substance, application and positioning of the core elements 211 within the article 20 may be simplified. The core elements 211 may be applied separately or via separate sub-processes. The core elements 211 may also come from the same source or web of absorbent material and may be applied generally together via the same sub-processes with one core element being flipped, rotated, or otherwise further manipulated to reach its ultimate position adjacent the other core element 211.

Referring specifically to FIG. 2C, the resultant, two-element, absorbent core 210 features, therefore, a narrow mid-section or central region M0 that is positioned proximate the lateral centerline XX in the crotch region 214. This narrowing of the central region M0 translates to improved user comfort as well as compatibility with the leg sealing components of the absorbent article 20. The greater amount of absorbent material per unit of area in the narrower central region M0 and more specifically, in the multi-layered section 250, provides greater or increased absorbency in the portion of the absorbent article 210 that has the greatest need for it. Accordingly, the multi-layered section 250 may be referred to as the primary absorbent region 250. Also, the resultant absorbent core 210 is wider upward from the crotch region 214 toward the front and rear longitudinal ends 207a, 207b (i.e., the upper absorbent regions). This increased expanse of core material increases the absorbent coverage in these upper regions of the absorbent article 210. The extra core material also helps to seal and prevent leakage in and from the waist regions 213 of the article 210.

To facilitate the present description, the absorbent core 20 may be described as having a narrow central region or midsection M0, and a pair of end regions E1, E2 on opposite sides of the central region M0. The locations or bordering of these regions are only generally defined (for purposes of the present description). In various embodiments, the primary absorbent region 250 is situated substantially in the central region M0, but may extend longitudinally into the end regions E1, E2. The end regions E1, E2 may also be referred to as upper absorbent regions as these regions are generally positioned above the central region M0 when the absorbent article is in use.

Figure 2E:
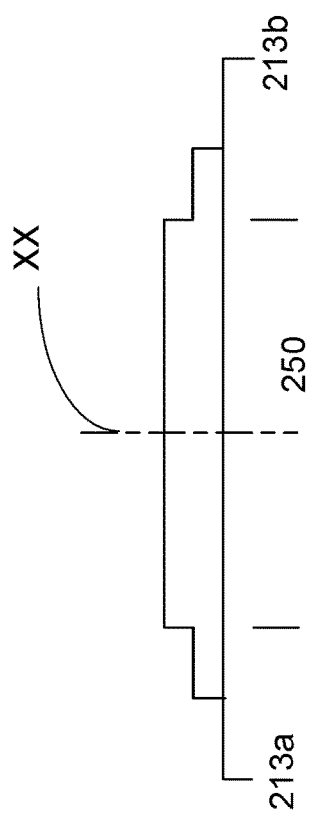
FIG. 2E is a cross sectional view illustrating a lateral absorbent profile of the absorbent article in FIG. 2A, across lines 2E-2E.

The graphical illustration of FIG. 2D illustrates the increase and decrease in the concentration of absorbent material in the absorbent article 20 along the longitudinal centerline YY from one waist end region 213a to the other waist end region 213b. This graphical illustration represents, therefore, the longitudinal absorbency profile of the article 20 from one end 212a to the other end 212b. The illustration also helps describe profiled cores according to the present invention as an absorbent construction having marked variations in absorbency (absorbent capacity per unit area (e.g., square inch) or absorbent densities) along specified directions or at specified locations on the central body 205. As explained above, the greater concentration of absorbent material provided by the two layers of core elements 211a, 211b provide high absorbency at the crotch region 214 of the absorbent article 20. The absorbent article 210 also exhibits absorbency per unit area near the waist regions 213a, 213b as imparted by the end regions E1, E2 of the core 210, although it is significantly decreased from that which characterizes the primary absorbent region 250. Nevertheless, the core elements 211 extend sufficiently upward into the waist regions 213a, 213b to expand and extend the absorbent coverage of the article 210. Beyond the absorbent core 210, the absorbency (and absorbency per unit area) of the disposable absorbent article 20 drops off significantly as expected. FIG. 2E illustrates the lateral absorbency profile of the core 210 along a lateral direction demarcated by the line LL-LL in FIG. 2A. This line LL-LL is actually located below the lateral centerline XX. The lateral absorbent profile illustrates a relatively narrow absorbent region with relatively high absorbency and/or absorbent density.

In the descriptions provided herein, the inventive core may be described as a profiled core. In the present context, this description relates to the varying absorbency imparted upon the absorbent article along specific directions or at specified locations on the central body. It also refers to the varying physical contour of the resultant absorbent core—which is illustrated by the absorbent profiles in FIGS. 2D and 2E. It should be noted that in some applications, variation in absorbent densities may be achieved by using core materials of different absorbent properties in lieu of, or in addition to core materials of substantially similar absorbent properties.

In developing the various configurations provided herein, optimal use of absorbent materials is an important design consideration. A balance is often struck between achieving high absorbency in the article and maintaining low material cost. This also requires controlling over use and over concentration of absorbent material so as to prevent lumps from forming or cause components to impinge upon the user's skin, thereby compromising the comfort of the user. Without care, an irregular core profile may also negatively impact the shape of the absorbent core when worn and lead to stressing the leakage prevention mechanisms of the article (e.g., elasticized leg cuffs and leg gathers). Thus, aside from cost considerations, the absorbent profiles proposed are not simply the result of laying out as much absorbent material as possible.

As discussed above, the design considerations accounted for also include manufacturability and ease of assembly. Very often these attributes translates to cost efficiency in the resultant product, as well as increased quality of construction. In this respect, the present invention achieves improved product designs, including configurations that achieve specific absorbent properties and/or specific shapes without sacrificing or burdening manufacturability. One feature of the invention that helps achieve these objectives is the use of substantially identical core elements to create various core shapes, including irregular shapes (e.g., non-rectangular), and absorbent profiles. The selection of core elements also provides design and manufacturing flexibility as FIG. 2C helps to illustrate.

As an example, the inventive configuration and selection of core elements 211 allow the manufacturer of the absorbent article 20 to readily vary or fine tune the shape of the absorbent core 210 and disposable absorbent article 20 by adjusting the distance X between the longitudinal end 217a of the first core element 211a and the longitudinal end 217b of the second core element 211b. In this way, the overall length L of the absorbent core 210 may be adjusted to accommodate different size absorbent articles. Such a linear adjustment may be easily made in a substantially linear assembly process of the absorbent core. This adjustment also allows desired lateral or longitudinal absorbent profiles to be achieved, including enlarging or reducing the primary absorbent region. The manufacturer can also make further modifications to the absorbent profile and the overall dimensions of the core by adjusting the length C and widths A and B of the individual absorbent core elements.

Figure 3B:
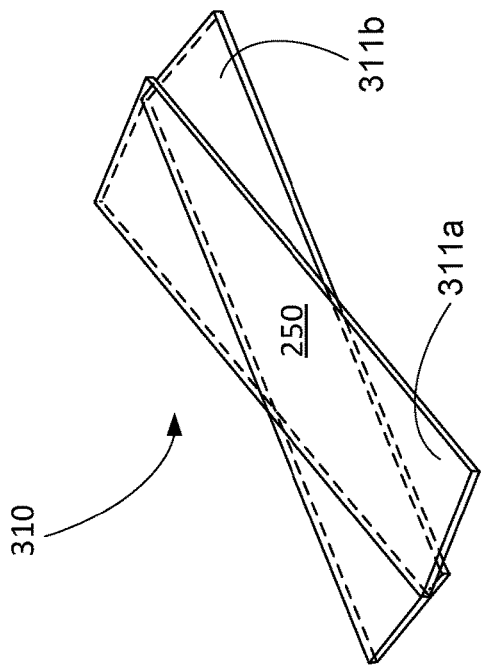
FIG. 3B is an isolated perspective view of the absorbent core in the disposable absorbent article in FIG. 3A.
Figure 3A:
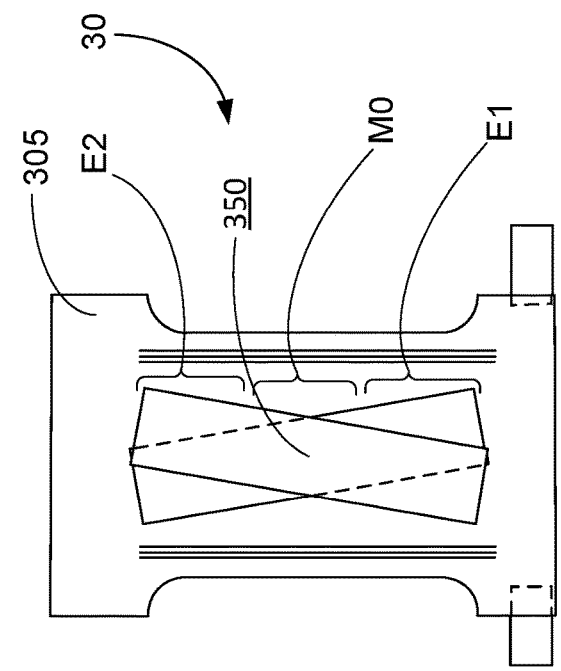
FIG. 3A is a simplified plan illustration of yet another embodiment of a disposable absorbent article according to the present invention.

FIGS. 3A and 3B illustrates an alternately profiled absorbent core 310 utilized in an absorbent article 30 and composed of identical absorbent core elements 311a, 311b having an alternate shape (wherein like elements are referred to using like elements). In this embodiment, a first, rectangular shaped absorbent core element 311a is partially overlaid or superimposed over at least a second rectangular shaped absorbent core element 311b to produce an absorbent core 310 of a different shape and absorbent profile. Key features of this embodiment again include a lateral narrowing of a mid section M0 of the absorbent core 310 to achieve a near hourglass shape. The longitudinal position of this narrow mid section M0 can be varied by displacing one of the rectangular shaped core elements 311 laterally relative to the second rectangular shaped core element 311. The inventive absorbent core 310 also provides laterally wider upper or end regions E1, E2 that saddle the mid section M0. The overlay of two core elements 311 also forms a dual layered primary absorbent region 350 in the central region M0, which displays a relatively greater concentration of absorbent material. In this embodiment, the primary absorbent region 350 extends all the way through the length of the end regions E1, E2.

Figure 4B:
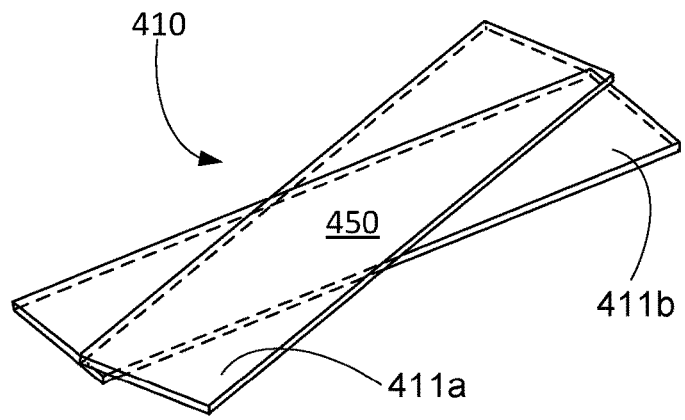
FIG. 4B is a perspective view of the absorbent core in FIG. 4A.
Figure 4A:
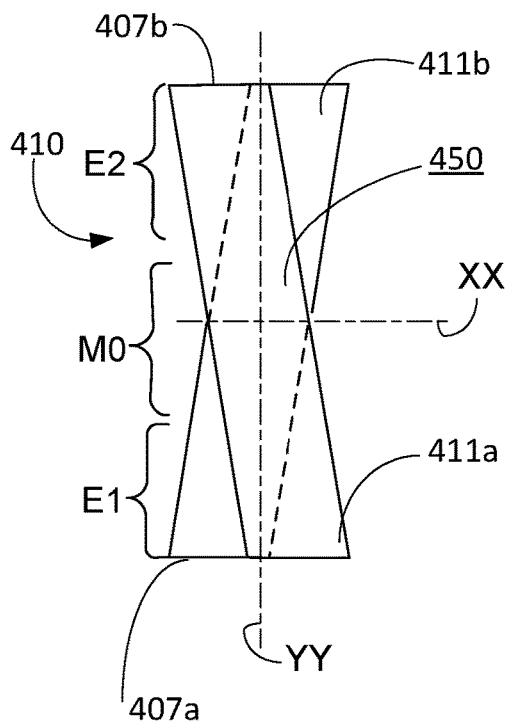
FIG. 4A is a simplified plan illustration of an absorbent core according to yet another embodiment of the present invention.

FIGS. 4A and 4B depict an alternative absorbent core 410 that is a further variation of the absorbent cores 210, 310 described above. The absorbent core 410 is produced from two non-rectangular, irregularly shaped absorbent core elements 411a, 411b but, in this embodiment, each core element 411 has a parallelogram shape. These core elements 411a, 411b are superimposed to produce a longitudinally and laterally symmetric absorbent core 410 (symmetric about the longitudinal and lateral centerlines YY, XX). With this configuration, the longitudinal ends 407a, 407b of the absorbent core 410 are defined by a single straight edge (spaced in parallel relation with the end edge of the absorbent article (not shown)). Thus, the end or upper absorbent regions E1, E2 of the core 410 are fairly uniform, and less likely to lump, impinge, pinch, or provide discomfort to the user. As with the absorbent core of FIGS. 3A, 3B, the absorbent core 410 features a primary absorbent region 450 that can extend from the central region M0 into the upper absorbent regions E1, E2.

Figure 5A:
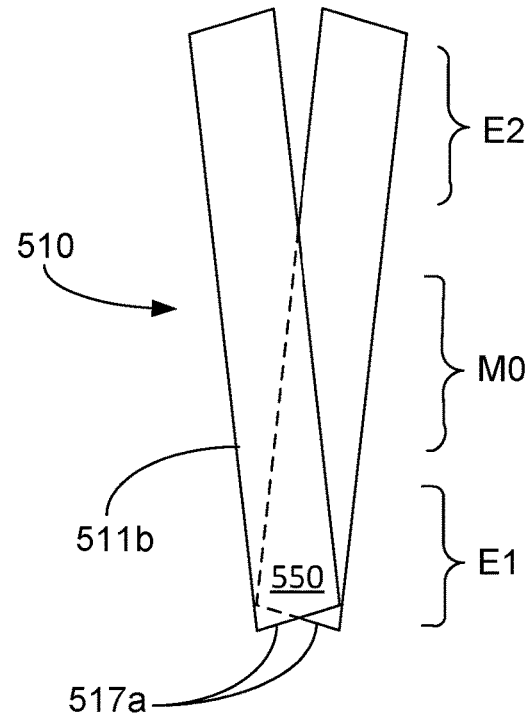
FIG. 5A is a simplified plan illustration of an absorbent core according to yet another embodiment of the present invention.
Figure 5B:
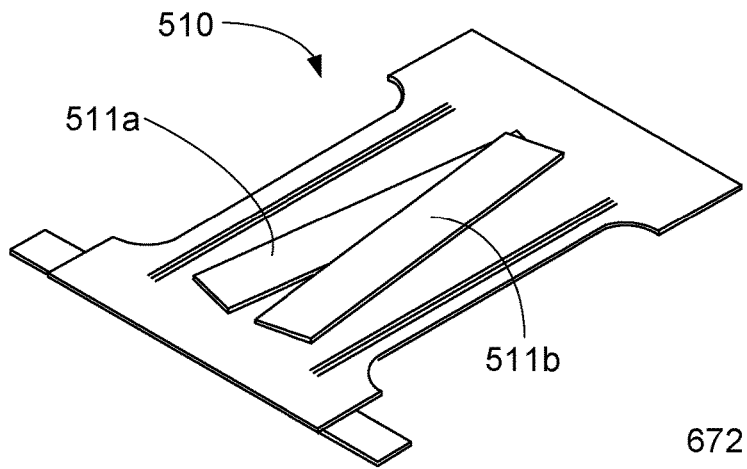
FIG. 5B is a simplified plan illustration of a disposable absorbent article employing an absorbent core, according to yet another embodiment of the present invention.

In yet another aspect of the present invention, an absorbent core 510 is achieved utilizing a pair of non-symmetrical absorbent core elements 511a, 511b as shown in FIGS. 5A and 5B. The core elements 511a, 511b are provided in either rectangular or parallelogram shape and together form an absorbent core 510. In this embodiment, the two core elements 511a, 511b are superimposed proximate mutually adjacent ends 517a rather than centrally. This overlay produces a generally kite shaped primary absorbent region 550 suitable for incorporation into a disposable absorbent article 50 such as that shown in FIG. 5B. Thus, the resultant absorbent core 510 is characterized as having greater concentration of absorbent material at one end region E1 (also greater absorbent density), and a lower concentration but wider expanse of absorbent material at an opposite end region E2, and a longitudinal absorbent profile reflecting same. In between, the absorbent core 510 still exhibits a narrow central region M0.

It is anticipated that an absorbent core of this type may be utilized in a baby diaper construction with the end region including the primary absorbent region being presented to the front of the wearer, thereby positioning a region of high absorbency to receive liquid exudates, and a wider absorbent region presented to the back of the wearer to provide better containment of solid exudates. In addition, the two absorbent core elements 511a, 511b may be arranged to present a v-shaped recess in the back of the diaper, thereby providing a containment pocket for feces collection.

In alternative embodiments, the core elements may be modified with angled edges (as longitudinal ends). The edges of adjacent core elements can cooperate to present a straight edge at the front or rear ends of the core, in a manner similar to that provided in the parallelogram shaped core elements 411 of FIGS. 4A, 4B.

FIGS. 6 through 9 illustrate alternative absorbent articles embodying various aspects of the invention, including absorbent cores of advantageous designs. More particularly, these alternative embodiments illustrate another mode of achieving advantageously shaped and advantageously profiled absorbent cores, and disposable absorbent articles with distinct absorbent profiles. In one aspect of the present invention, elastic materials are attached to, or otherwise incorporated into, the absorbent core element(s) to generate inventive absorbent core constructions.

Figure 6A:
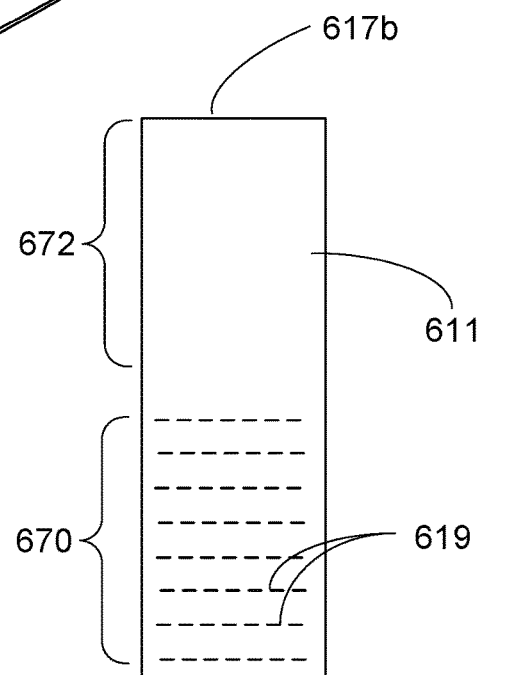
FIG. 6A is a simplified illustration of an absorbent core according to yet another embodiment of the present invention, in a pre-tensioned state.

Referring first to FIG. 6A, an absorbent core element 611 is initially provided having a generally rectangular shape and a pair of longitudinally spaced apart ends 617a, 617b. A suitable, tensioned elastomeric material 619 is selectively applied on or within the absorbent core element 611 at various points or locations near the first end 617a. The elastomeric material 619 is oriented lengthwise in the lateral direction. Suitable elastomeric materials include, but are not limited to, elastic strands, elastic films or elastomeric adhesives. As shown in FIG. 6A, the elastomeric material 619 is preferably an elongated elastic element, such as an elastic strand. The applied elastomeric materials are referred to simply as elastic elements or elastics. The selected attachment points preferably make for a predetermined pattern that describes multiple, laterally-oriented rows of elastics 619 at even pitch, as shown in FIG. 6A. Accordingly, the applied pre-tensioned elastics impart an elastic force in the generally lateral direction across the absorbent core element 611.

Figure 6B:
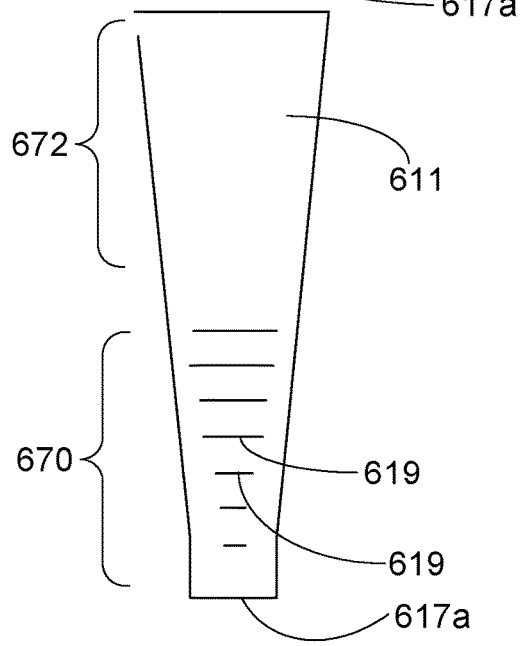
FIG. 6B is a simplified illustration of the absorbent core in FIG. 6A in a relaxed or contracted state.

Preferably, the rows of elastics 619 are concentrated in a region 670 proximate one longitudinal end 617a of the core element 611 (i.e., a substantially elasticated end region 670). While this longitudinal end region 670 of the core element 611 is substantially incorporated with elastics 619, the opposite end region 672 is substantially clear of elastomeric elements (i.e., non-elasticated). FIG. 6B depicts the absorbent core element 611 in a relaxed state. Releasing the elastics 619 from tension allows the elasticated region 670 to substantially contract and narrow (relative to other regions), and the rectangular shaped core element 611 to deform to near trapezoidal shape.

FIG. 6C depicts an absorbent article 60 employing a pair of the absorbent core elements 611 and a resultant absorbent core 610 having an advantageously hourglass shape and unique absorbent profile. The absorbent profile of the core element 611 reveals higher concentration of absorbent material in the area of the elasticated core region 670 due to the contracted core material. A first absorbent core element 611a is positioned over a second, substantially similar absorbent core element 611b to define a narrow, substantially elasticated central region M0 and wider generally non-elasticated end regions E1, E2. As previous embodiments have demonstrated, the inventive configuration also provides a greater concentration of absorbent material (greater absorbent density) in the central region M0 of the absorbent core 60 than in the end regions E1, E2. The elasticated core region 670 defined in this embodiment substantially corresponds with the primary absorbent region 650 described in previous embodiments. The primary absorbent region 650 is therefore, defined by both higher absorbent capacity per unit area as imparted by the multiple layers of absorbent material and high contraction due to the high concentration of elastics 619.

The cross-sectional view of FIG. 6D reveals a central region M0 not only composed of multiple core layers, but of layers of core material that are more highly concentrated. The contraction of the core elements 611a, 611b creates undulations in each core element 611a, 611b, producing yet another unique physical profile and unique absorbent profile. Generally, the contraction of the core material produces a core element of greater average thickness. Further, the stacking of one core element over another core element with undulations produces a thicker and larger (in volume) absorbent core. The core includes voids or spaces S0 between the core elements 611a, 611b and between the top core element 611a and the topsheet 602 (or A/D layer). The contracted core material also provides channels C1 that function as acquisition and distribution channels for the absorbent core 610 and ridges P alongside the channels C1. The channels C1 help capture liquid exudates, for example, and disperse the liquids over a greater area of core material. FIG. 6D also shows an additional, supplemental layer 639 of a non-woven or core material below each of the core elements 611a, 611b. The supplemental layer 634 is provided to promote and provide adhesion between the core material and the elastics 619. In the cross-sectional view of FIG. 6D, the supplemental layer 639 resides below the elastics 619.

FIGS. 6E and 6F illustrate a variation of the inventive absorbent core elements in FIGS. 6A to 6D (wherein like elements are indentified using like reference numerals). In one embodiment, the tension placed on the elastics 619' during attachment to the absorbent core element 611' is increased. When the elastics 619' are released, the core material contracts even more to produce an elasticated region 670' having an overall area that is reduced relative to that in the embodiment shown in FIGS. 6A to 6D. A differently shaped elasticated region 670' may be produced by selecting a different type of elastic or an elastic of different shape and length. A different shape, particularly the curvature, may also be created by changing the tension denier of the elastic strand, changing the number of or the pitch between elastics, and/or by altering the position of the elastic(s) (e.g., varying the distance between successive elastics). In this embodiment, the resulting absorbent core 610' has a narrower and more pronounced central region M0. The central region M0 takes on a more curved or concave shape at the transition between the elasticated region 670' and the end regions E1, E2.

FIGS. 7A and 7B depict yet a further embodiment of the present invention, wherein an absorbent core is provided with a single core element 711. An alternatively shaped absorbent core or core element 711 is produced via the selective placement and attachment of elastic elements 719 within the core material, beneath the core element, or on top of the core element. By selective placement of elastic strand or other elastomeric materials, the relative width of the core element 711 in these areas is reduced, as discussed above. FIG. 7A shows one such embodiment of this core, with pre-tensioned, extended elastic strands 719 secured to the absorbent core element 711 in a central elasticated region 770. When tension is released, the width of the absorbent core element 711 is substantially reduced as shown in FIG. 7B, creating a narrow elasticated material region M0.

FIGS. 7C and 7D depict yet another embodiment in which an absorbent core element 711 provides an absorbent core with an elasticated central region M0. Elastics 719 are applied to the core element 711 in the same laterally extended fashion. The elastics in this embodiment are arranged in rows of varying pitch, however, to achieve a specific shape. Preferably, the elastics 719 near the lateral centerline XX are spaced closer together, while the elastics 719 farther away from center are spaced further apart. The area near the lateral centerline XX is, therefore, more elasticated than areas beyond. This results in an absorbent core 711 having a more gradually narrowed or curved central region M0. By varying the pitch in this manner, the curved shaped of the narrowed central region may be adjusted further.

FIGS. 8A through 8E illustrates yet another aspect of the invention, in which elastic elements 819 are introduced between, above, within or below multiple layers of absorbent core elements. FIG. 8A provides a simplified illustration of an absorbent core construction 810. Pre-tensioned elastic elements 819 are first disposed beneath a first elongated absorbent core element 811a and attached thereto. The elastics 819 in this exemplary embodiment are centrally located respective of the first core element 811a, and are spaced at a consistent pitch. The Figures show elastic strands employed as the elastics 819; however, elastic materials such as elastic film, elastic adhesive or elastic nonwovens may be used to achieve similar effects.

Referring also to the view in FIG. 8B, a second absorbent core element 811b is provided and then deployed on top of the first absorbent core element 811a. The generally rectangular second absorbent element 811b is cut appropriately shorter (and perhaps, reduced in width also) to correspond with the dimensions of the desired primary absorbent region and/or desired absorbent profile. The elastics 819 and the dual layer of absorbent core elements 811a, 811b are bonded using any suitable bonding means, such as hot melt adhesives, ultrasonic bonding or through the fusing of thermoplastic fibers by heat. It is a desirable, but not necessary, feature of this invention that at least one of the absorbent core elements 811 (i.e., the top absorbent core element 811b in FIGS. 8A, 8B) is slit or cut at multiple locations (producing slits 873). As shown in the Figures, the top absorbent core element 811b preferably contains multiple slits 873. The slits 873 are generally aligned in the lateral direction and, in this embodiment, staggered in rows of two and three slits. The slits 873 preferably penetrate entirely through each layer of absorbent material, and in some embodiments may have a length of between 1-50 mm. It is envisaged that the invention also allows for further layers of slit or unslit absorbent material (core elements), elastic materials, fluid handling materials such as acquisition layers or surge layers, tissue layers, nonwoven layers or film.

Both FIGS. 8A and 8B depict the shape of the absorbent core 810 prior to release of the elastics 819 from tension. FIG. 8C depicts the absorbent core 810 after the elastics 819 are released. The width of the absorbent core 810 in an elasticated central region M0 is substantially reduced, particularly more so around the lateral centerline XX where the elastics 819 are gathered. Further, the laterally aligned slits 873 disposed on the top core element 811b are caused to open up and create voids 875 within the core element 811b. These voids 875 provide passages that facilitate flow of fluid into lower levels of the core construction (e.g., the first core element 811a) of the absorbent core 810.

FIG. 8D depicts an alternative absorbent core 810' that achieves a slightly different shape by arranging the rows of elastics 819 by arranging the elastics 819 at a higher pitch (than in FIGS. 8A, 8B). This arrangement produces a smoother curved central region M0. FIG. 8E illustrates a variation of the core construction described in FIGS. 8A-8C. In this alternative absorbent core 810", the pre-tensioned elastic elements 819 are disposed between the two absorbent core layers 811a, 811b (rather than below the bottom core element 811a). As previously discussed, it is possible for the elastics to be distributed, above, below, within or between any of the layers of the absorbent core. In some embodiments, the elastics are preferably positioned within or between layers to promote adhesion.

Figure 9B:
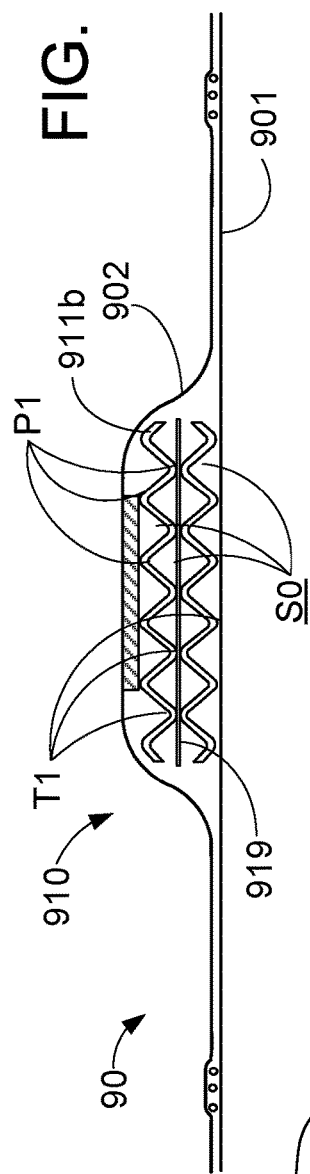
FIG. 9B is a cross-sectional view of a disposable absorbent article utilizing the absorbent core in FIG. 9A.

FIG. 9A illustrates yet a further aspect of the present invention. The elasticized, accordion-shaped absorbent core construction 910 is produced using two absorbent core elements 911a, 911b and elastic elements 919. Notably, the longitudinal centerline YY or longitudinal direction of the absorbent article is identified as being perpendicular to the elastics 919. FIG. 9B is a lateral cross-sectional view of disposable absorbent article 90 utilizing the absorbent core 910 with the cross-section aligned along a single laterally extending elastic 919. A series (or layer) of pre-tensioned elastic elements 919 is disposed between a first or bottom absorbent core element 911a and a second or top absorbent core element 911b. The two layers of core elements 911a, 911b and the pre-tensioned elastic elements 919 are bonded at predetermined locations along the lateral extent of the tensioned elastic 919. The bonding locations are preferably equally spaced apart. In this specific embodiment, the bonding locations actually make longitudinally extending bonding strips 930 that run generally, continuously across the rows of laterally oriented elastics 919. Thus, between two elastics 919, the core elements 911a, 911b may be bonded directly to one another. Between the bonding strips 930, the core elements 911a, 911b remain un-bonded. Bonding may be achieved using hotmelt adhesives, ultrasonic bonding, through the fusing of thermoplastic materials by heat, or by any other suitable means.

The clearly defined bonding strips 930 are generally perpendicular to the direction of elasticity (lateral direction in this embodiment). Accordingly, when tension on the elastics 919 is released, the core elements 911a, 911b contract with the elastics 919 on both sides of the bonding strips 930. In the un-bonded areas between the bonding strips, the un-restrained portions of the core element rise to create peaks or ridges P1. As shown in FIGS. 9A and 9B, troughs Ti are also produced between the ridges P1 and along or about the extent of the bonding strips 930. The resultant absorbent core 910 provides, therefore, an accordion like structure defined by a regular series of peaks P1 and troughs Ti. As further shown in FIG. 9B, the accordion-shaped core 910 features an abundance of laterally extending voids or spaces S0 between the core elements 911a, 911b and between top core element 911b and the topsheet 902.

An important benefit of the resultant structure is that the inventive core construction achieves loftiness (i.e., which promotes comfort and softer regions) and void space out of an otherwise flat core and without significant void volume. The added void volume serves to provide a temporary fluid holding and fluid transporting space. This space provides the fluid a place within the confines of the diaper to temporarily reside during the few seconds it takes for the superabsorbent to activate and permanently lock up the fluid. The troughs Ti and the voids or spaces S0 above the troughs Ti channels, and facilitate dispersal of fluid exudates.

FIGS. 10A-10H depict absorbent core constructions embodying further aspects of the present invention. These absorbent core constructions provide ergonomically-shaped cores that enhance the fit and sealing capabilities of the resultant disposable absorbent article. In particular, the design of the absorbent core constructions target an absorbent core having a nearly hourglass shape and an advantageous absorbent profile. Regarding the absorbent profile, the inventive absorbent core constructions in these Figures illustrate means for distributing absorbent core material in an optimized, non-uniform manner in and along the central body of the disposable absorbent article.

Referring first to FIGS. 10A and 10B, a single layered core element 1011 is provided in a generally rectangular, elongated shape, which can be described as having longitudinal and lateral centerlines YY, XX, first and second longitudinal ends 1017a, 1017b, and right and left side margins 1006a, 1006b, respectively. In accordance with the invention, the core element 1011 is marked by a pair of generally lateral cuts or slits 1008 that originate at and extend from, the right margin 1006a. The slits 1008 preferably terminate proximate the left margin 1006b but are spaced sufficiently therefrom to prevent compromising the structural soundness of the core element 1011. Each of the slits 1008 is preferably spaced the same distance from the proximate longitudinal ends 1017a, 1017b. The slits 1008 help define the three sections of the core element 1011: a top section or flap 1003; a middle or mid section 1004; and a bottom section or flap 1005.

In one aspect, each of the slits 1008 is sufficiently long to allow the adjacent flap 1003, 1005 to bend and pivot away from the mid section 1004, as illustrated in FIG. 10B. The top and bottom flaps 1003, 1005 are preferably displaced in this manner and, at an acute angle from the midsection 1004. As necessary, the width and shape of the slits 1008 may be enlarged and/or the left side margin 1006b provided with cut-outs proximate the slit 1008 to accommodate the rotation of the flaps 1003, 1005 and compression of the area along the side margin 1006b.

Figure 10E:
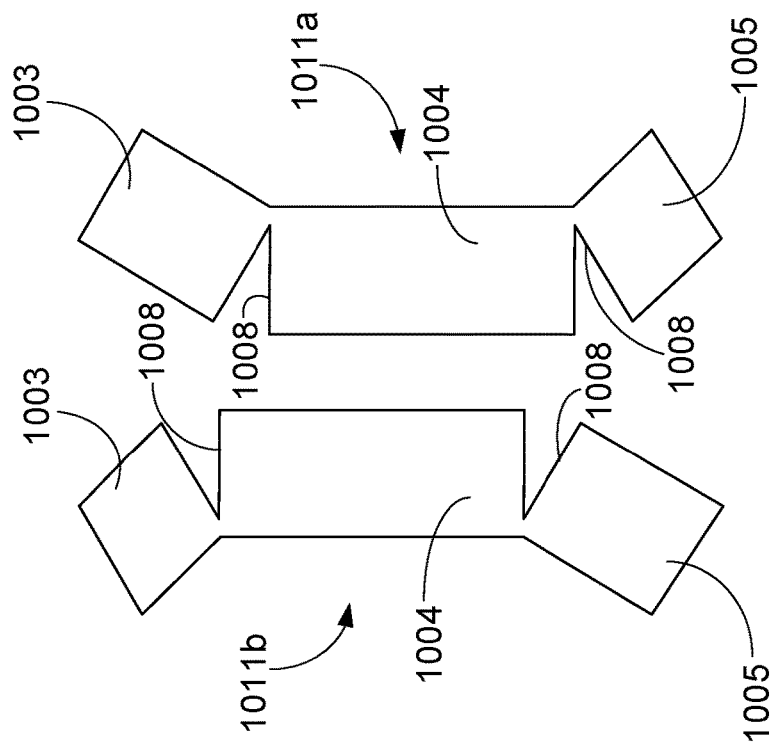
FIG. 10E is a simplified plan illustration of a pair of absorbent core elements utilized in an alternative absorbent core, according to the present invention.
Figure 10C:
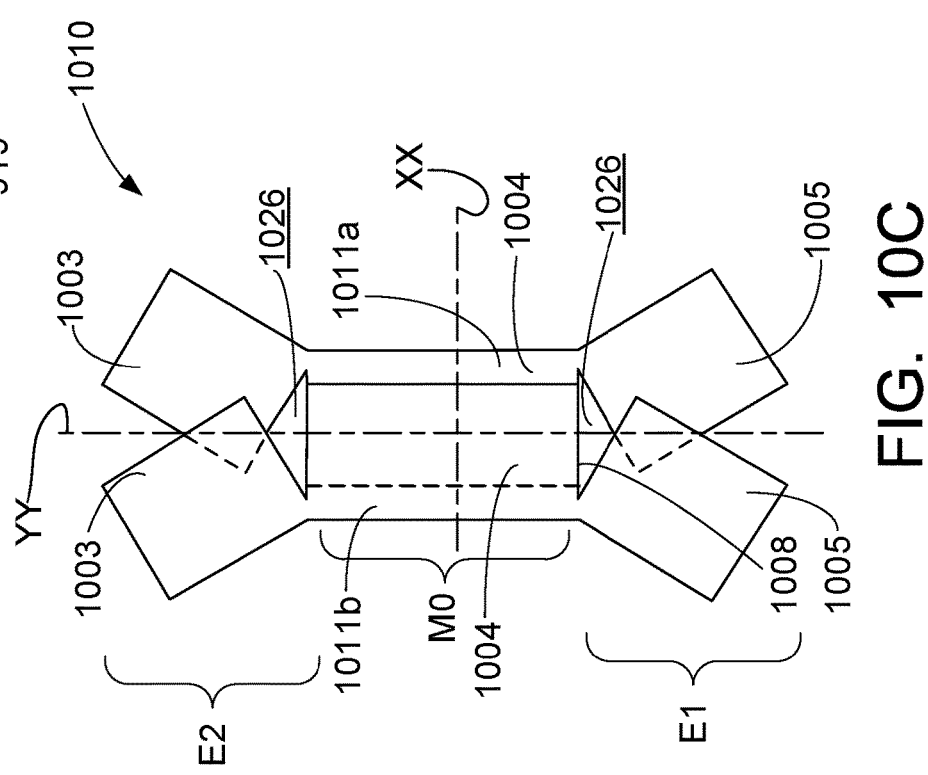
FIG. 10C is a simplified illustration of an absorbent core utilizing the absorbent core elements in FIG. 10A, as shown in an applied state.

Now turning to FIGS. 10C and 10D, an advantageous absorbent core construction 1010 is created through cooperation of two substantially similar core elements 1011 of the type depicted in FIGS. 10A-10B. For purposes of the description, one core element 1011 may be referred to as a first or right core element 1011a, and the other core element 1011b as a second or left core element 1011b. The two core elements 1011 are substantially similar and the components of the two core elements 1011 are referred to using like reference numerals. The two core elements 1011a, 1011b are placed adjacent one another in a manner whereby the slits 1008 are laterally aligned and substantially co-incident. The core elements 1011a, 1011b are preferably spaced the same distance from a longitudinal centerline YY. With this placement, each of flaps 1003 or 1005 oppose a corresponding flap 1003 or 1005 and is displaced and rotated away from the longitudinal centerline YY. This creates an open section or recess 1026 above the slits 1008. There is some overlap between each opposing pair of flaps 1003, 1005, however, and, in the context of the resultant absorbent core 1010, each pair of opposing flaps 1003, 1005 cooperate to form one of two flared and widened end region E1, E2.

As also shown in FIG. 10C, midsections 1004 substantially overlap and mutually cooperate to create a highly absorbent central region M0 of the resultant absorbent core 1010. Preferably, the central region M0 is aligned symmetrically about both the longitudinal centerline YY. As also shown in FIG. 10C, the central region M0 is substantially narrower than the end regions E1, E2. It is an advantageous feature of this embodiment that the transversely displaced pairs of flaps 1003, 1005 are displaced outwardly, and slightly rotated, to help form the generally hour glass shape of the absorbent core 1010. In yet another advantageous aspect, the flaps 1003, 1005, and the slits 1008 that help to define these sections, can readily interrelate and interlock to facilitate cooperation between the core elements 1011. This interlocking feature helps to stabilize the resultant absorbent core 1010 and to positively place and shape the end regions E1, E2 according to the desired design. In specific applications, this interlocking relationship helps to guard against any bias in the end regions E1, E2 to return toward the longitudinal centerline YY.

FIG. 10D illustrates an optional and further configuration utilizing the core elements 1011 in FIGS. 10A-10C, wherein like elements are again referred to using like reference numerals (as previously used in respect to FIGS. 10A-10C). This further configuration addresses possible shortfalls in the configuration previously described. Referring to FIG. 10D, a resultant absorbent construction 1010a utilizes a third core element 1011c. Generally, the third core element 1011c provides a substantially rectangular layer of absorbent material to add to the central region M0. The third core element 1011c in this embodiment is made longer than the mid-sections 1004, so as to cover any undesirable areas of low or substantially nil absorbency. In particular, the third core element 1011c is shaped and positioned to extend over the previously open recess 1026 in FIG. 10C (see FIG. 10C), thereby covering the recess 1026.

The third core element 1011c also enlarges the primary absorbent region 1050 of the absorbent core, increasing its absorbent capacity. It is noted, however, that in other embodiments, it may not be desirable to increase the thickness or absorbency of the primary absorbent region (to minimize cost and manufacturing complexity, for example). In such cases, the thicknesses of the third core element and the other core elements may be adjusted to minimize the overall thickness of the central region. In the illustration of FIG. 10D, this third core element 1011c is shown positioned between the other two core elements 1011a, 1011b. In further embodiments, the third core element 1011c may be positioned above or below both core elements 1011 (as the top-most or the bottom-most layer of absorbent material).

FIGS. 10E and 10F illustrate yet a further configuration and variation of the invention, wherein first and second absorbent core elements 1011a, 1011b provide the components of yet another resultant absorbent core 1010b (see FIG. 10F). This resultant absorbent core 1010b features an alternative means for increasing the absorbency in regions of nil and substantially nil absorbency. Each of the core elements 1011a, 1011b is again provided with a pair of lateral slits 1008 that help define a top flap 1003, a midsection 1004, and a bottom flap 1005. In this embodiment, the top and bottom flaps 1003, 1005 are not substantially identical. For the first core element 1011a, the top flap 1005 is shorter than the bottom flap 1003. Thus, the top flap 1005 also provides a smaller area than the bottom flap 1003. In contrast, the second core element 1011b is provided with a top flap 1005 that is longer and thus larger, than the bottom flap 1003. Now referring to FIG. 10F, core elements 1011a, 1011b are placed in a mutually cooperative relationship to form the desired absorbent core 1010b. As in other embodiments, this cooperative relationship provides a substantially dual-layered, narrow central region M0. The combination of core elements 1011a, 1011b also forms end regions E1, E2. As best illustrated in FIG. 10F, the overlapping of the various regions of the two core elements 1011, 1011b tend to cover the voids or regions of previously low or nil absorbency (see, e.g., recesses 1026 in FIGS. 10A, 10B). These regions of previously low or nil absorbency are reduced or eliminated by extending the longer flaps closer to center and overlapping the longer flap with the shorter opposing flap.

FIG. 10G illustrates yet another alternative configuration for an absorbent core 1010c in accordance with this embodiment of the present invention. FIG. 10G illustrates an alternative cooperation of two core elements 1011a, 1011b that achieves a particularly desirable interlocking relationship. The lateral slits 1008 of the core elements 1011a, 1011b, as well as the top and bottom flaps 1005, 1003, positively interlock the core elements 1011a, 1011b. As shown in FIG. 10G, the two flaps 1003, 1005 of the first core element 1011a are placed beneath the corresponding flaps 1003, 1005 of the second core element 1011b, while the mid section 1004 of the first core element 1011a is placed above or atop the corresponding mid section 1004 of the second core element 1011b. This positive interlocking relationship between the two core elements 1011a, 1011b aids stabilization of the resultant absorbent core 1010, and also, reduces or eliminates the use of adhesive to secure the core elements 1011a, 1011b together.

Figure 11A:
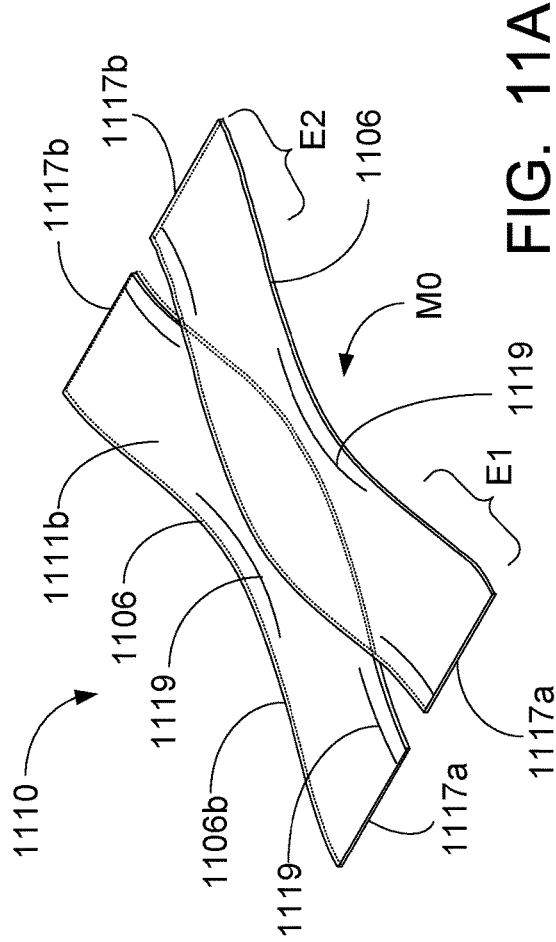
FIG. 11A is a simplified perspective illustration of an alternative absorbent core, according to the present invention.

FIG. 11A illustrates yet another embodiment of the present invention. In particular, FIG. 11A depicts an absorbent core 1110 that utilizes a pair of core elements 1111a, 1111b and exhibits a generally hourglass shape. The absorbent core 1110 features a narrow central region M0 that features a multi-layered primary absorbent region 1150 formed by mutual overlapping of the two core elements 1111a, 1111b. For purposes of description, the core elements 1111a are referred to as having longitudinal ends 1117a, 1117b, respectively and right and left side margins 1106a, 1106b, respectively. The absorbent core 1110 also provides substantially identical end regions E1, E2, both spaced longitudinally from the central region M0. The end regions E1, E2 have a lateral width that is greater than that of the narrower central region M0 of the absorbent core 1110. As with previous embodiments, the primary absorbent region 1150 is positioned about and extends from this narrow central region M0 of the absorbent core 1110. The resultant absorbent core 1110 exhibits, therefore, a nearly hour glass shape, having wider upper or end regions E1, E2 and a narrow central region M0. As explained in respect to previous embodiments, this nearly hour glass shape improves the fit and comfort of the disposable absorbent article, while enhancing the sealing capabilities of the article. It is noted that the core elements 1111a, 1111b utilized in this absorbent core 1110 have a more curved or S-shaped form. The core elements 1111a, 1111b are also slender than core elements of previously described embodiments. The resultant absorbent core 1110 has, therefore, a more aesthetically pleasing appearance and conforms well with the shape and configuration of the disposable absorbent article, before use and while in use.

In yet another aspect, the core elements 1111a, 1111b utilizes elastics 1119 which are situated at select locations. Selective and strategic placement of the elastics 1119 achieves the curved and S-shape form of each core element 1111a, 1111b. Notably, the elastics 1119 are oriented along a generally longitudinal direction at application, and are provided at a length generally short relative to the length of each core element 1111a, 1111b. As will be explained in more detail below, the longitudinally oriented elastic 1119 serves to contract and curve (concave) the surrounding areas, which coincides with a localized portion of the near side margins 1106 of the core element 1111. As a result, each elastic strand 1119 tends to make the longitudinal side margin 1106 of the core element 1111 concave about a point at or near the middle of the elastic 1119. To better illustrate how the curved shape of the core element 1119 is achieved, further reference is made to FIGS. 11B-11D, each of which illustrates a stage in the manufacture or assembly of the absorbent core 1110.

The source of the absorbent material is presented as an elongated continuous web 1180 of absorbent material (or core elements). A stretched elastic 1119 (i.e., in tension) is applied near the side margin 1106a or 1106b of the web and is preferably laminated thereabout to the absorbent material. Depending on the specific application, the length of the stretched elastic 1119 is typically a significant proportion of the length of the core. Each elastic 1119 is oriented along the longitudinal direction and spaced a short lateral distance from the near side margin 1106. For the illustrated embodiment, this lateral spacing is only about $1/10^{th}$ the width of the web 1180. Furthermore, the elastics 1119 are preferably intermittently applied along each side margin 1106a, 1106b. The longitudinal spacing elastics 1119 is preferably slightly larger than the stretched width of the individual elastics 1119, although it will be apparent to one skilled in the relevant art that the longitudinal spacing and the length of the elastics chosen will depend primarily on the size and degree of curvature targeted for the resultant absorbent core and absorbent article.

In the manner described, a series of elastics 1119 is applied near each side margin 1106 of the web 1180 of absorbent material. To achieve the configuration illustrated in FIG. 11A, the series of elastics 1119 along one side margin 1106a is preferably substantially identical to the other series or set along the other side margin 1106b. The intermittent period of the two series are, however, offset at one-half period intervals or 180 degrees. As shown in FIG. 11B, this means that along each lateral line across the web 1180 whereon an elastic 1119 is applied along one side margin 1106, that elastic 1119 is the only elastic applied. The area along the opposite side margin 1106 is clear and non-elasticized. Along the longitudinal direction of the web 1180, elastics 1119 are therefore applied alternately between one side margin 1106a and the other side margin 1106b. Accordingly, along the longitudinal direction, the web 1180 of absorbent material may be described as being alternately elasticized between one side margin 1106a and then the other side margin 1106b.

Figure 11D:
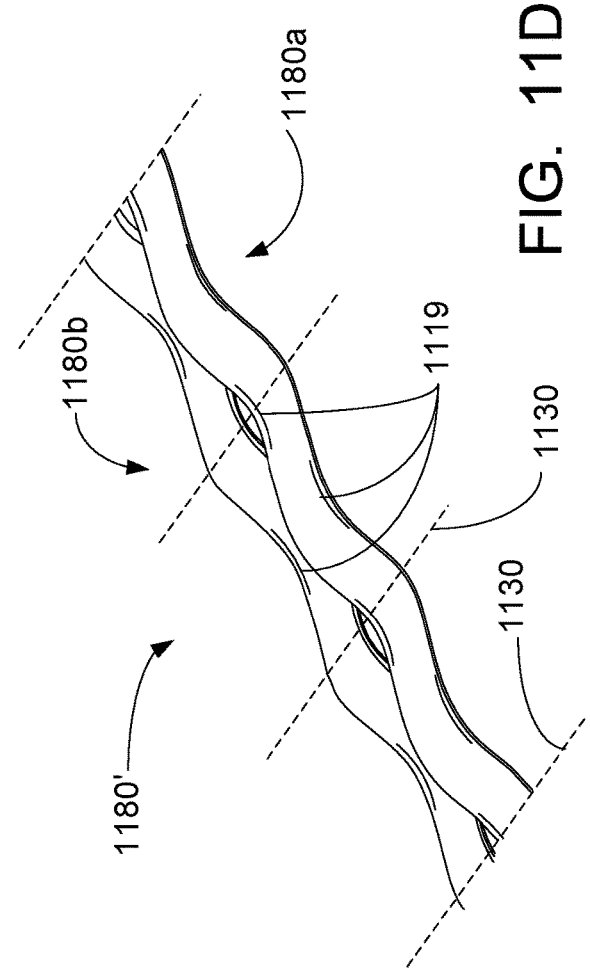
FIG. 11D is a simplified perspective illustration of a web or source of dual absorbent core elements of the type shown in FIG. 11C.
Figure 11B:
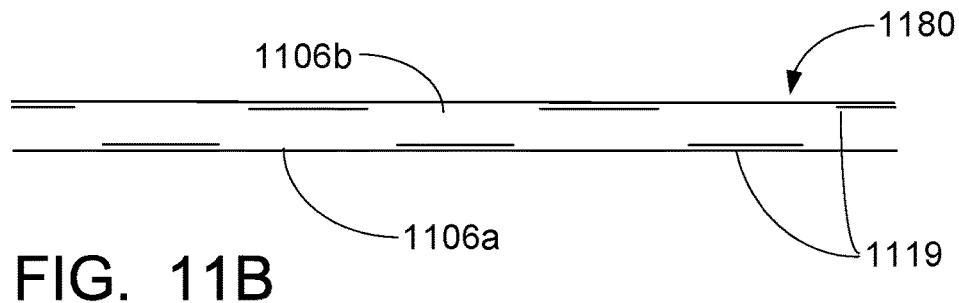
FIG. 11B is a simplified plan illustration of a source of elasticated absorbent core element shown in a tensioned state, according to yet another embodiment of the present invention.
Figure 11C:
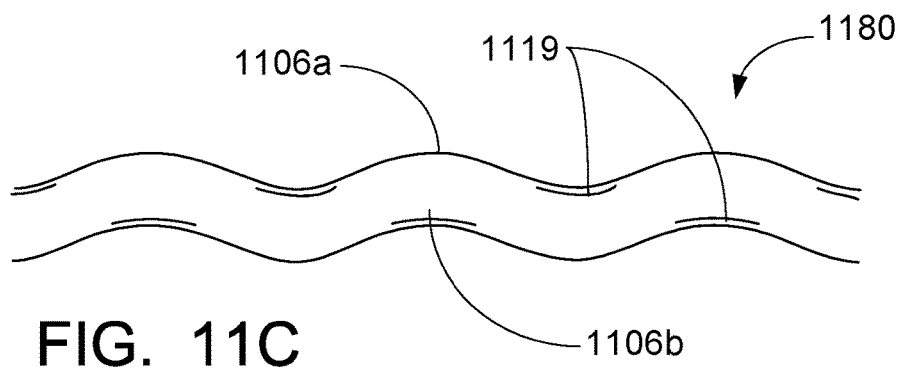
FIG. 11C is a simplified plan illustration of the source of absorbent core element in FIG. 11B, shown in a relaxed or contracted state.

After tension is removed from the elastics 1119, the regions around each elastic 1119 contract and the elastics 1119 draw the absorbent material into a gathered material as shown in FIG. 11C. Due to the contraction of the tensioned elastics 1119 and the distribution pattern of the elastics 1119 in alternate side regions, the absorbent web 1180 takes on a continuous S-shaped configuration. This S-shaped configuration provides alternate concave and convex curves. In this configuration, the elastics 1119 are present on the short sides or concave portions and the non-elasticized regions are found on the longer side or convex portions.

FIG. 11D depicts a continuous, dual web 1180' of absorbent core element consisting of two of the absorbent core webs 1180' described in FIGS. 11B and 11C. The web 1180' of absorbent core element is formed by overlapping a first web 1180a of continuous sinuosoidal-shaped (or "S-shaped") absorbent material with a second web 1180b of continuous S-shaped absorbent material. The two absorbent webs 1180a, 1180b are arranged in a non-parallel, opposed configuration such that the elastics 1119 are laterally aligned. The result is that the elastics 1119 on the two webs 1180a, 1180b alternate between being both on the inside side margins 1106 of the two absorbent webs 1180 and being both on the outside side margin 1106 of the two absorbent webs 1180. The resultant web 1180 also has alternating wide and narrow regions. This resultant web 1180 is then divided into individual absorbent cores 1110 by cutting through the transverse width of the core as indicated by lateral line 1130. The cuts are preferably made at the widest lateral portions which coincide where the elastics 1119 are both located along adjacent side margins 1106. These wide lateral portions, wherein the elastics 1119 are on adjacent margins 1106, provide the end regions E1, E2 of the resultant absorbent core 1110 (see FIG. 11A). The narrow lateral portions between these lateral wide portions, which overlap, become the narrow central region M0 of the resultant absorbent core 1110. This substantial overlap of webs 1180 in this narrow lateral portion also provides the primary absorbent region 1150 of the resultant advantageous absorbent core 1110.

Figure 11E:
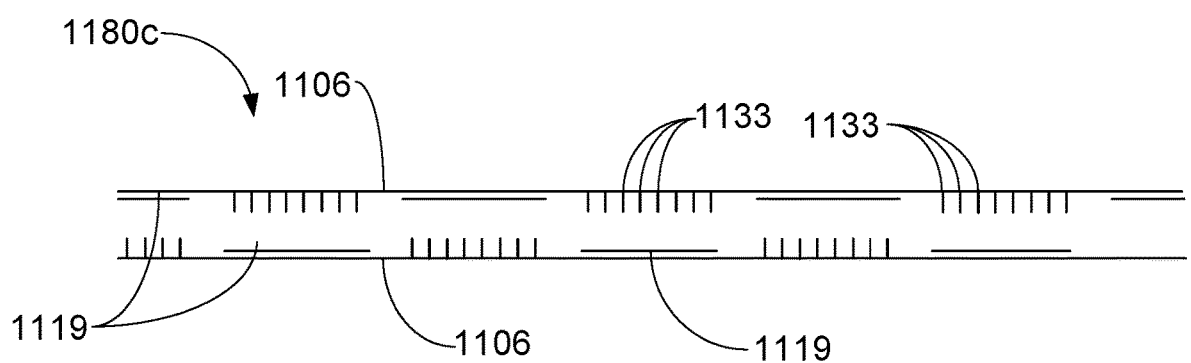
FIG. 11E is a simplified plan illustration of a web or source of alternative absorbent core elements according to yet another embodiment of the present invention, shown in a tensioned state.
Figure 11F:
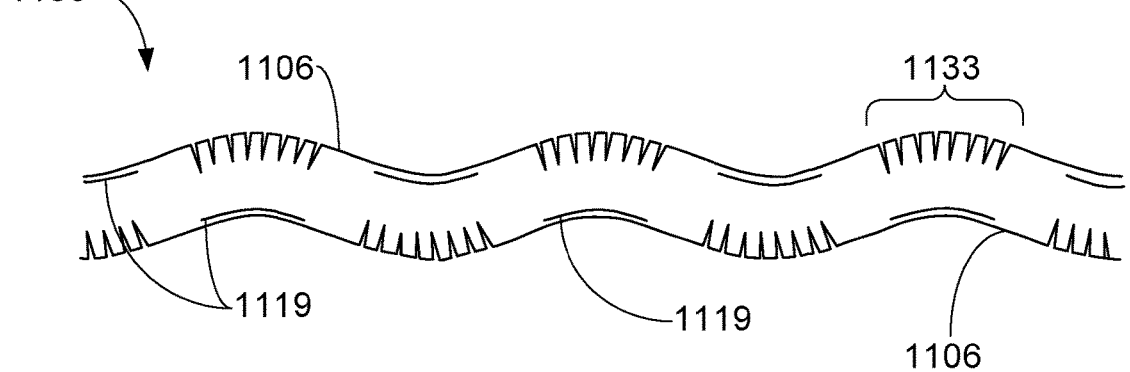
FIG. 11F is a simplified plan illustration of the web or source of absorbent core in FIG. 11E, as shown in a relaxed or contracted state.

FIG. 11E illustrates an alternate elongated web 1180c of absorbent core element. In this embodiment, slits 1133 are introduced to the web 1180 of absorbent core material to facilitate bending and flexibility of the individual core elements. The slits 1133 are preferably applied as groups of elastic, each group disposed primarily in the non-elasticized region of the core web 1180 (where the side margin 1106 extend and curve inward upon release of the elastics 1119). FIGS. 11E and 11F illustrate the web 1180 with multiple slits 1133 oriented in the generally lateral or transverse direction. The slits 1133 sever the non-elasticized portion of the near side margin 1106 of the web 1180. FIG. 11E depicts the web 1180 of absorbent material with the elastic elements 1119 under tension. When tension is released, the contraction of the elastic elements 1119 causes the surrounding region near the side margins 1106 to also contract. Meanwhile, the slits 1133 in the non-elasticized regions allow these regions near the side margin 1106 to extend more readily and provides a smoother curve. In certain embodiments, the length of the slits 1133 are less than ½ or ⅓ the lateral width of the web 1180. As a result, the web 1180 of absorbent material adopts a continuous S-shaped configuration, which is then used as a source web for a generally hourglass-shaped, elasticized core (see e.g., FIG. 11A).

Figure 12:
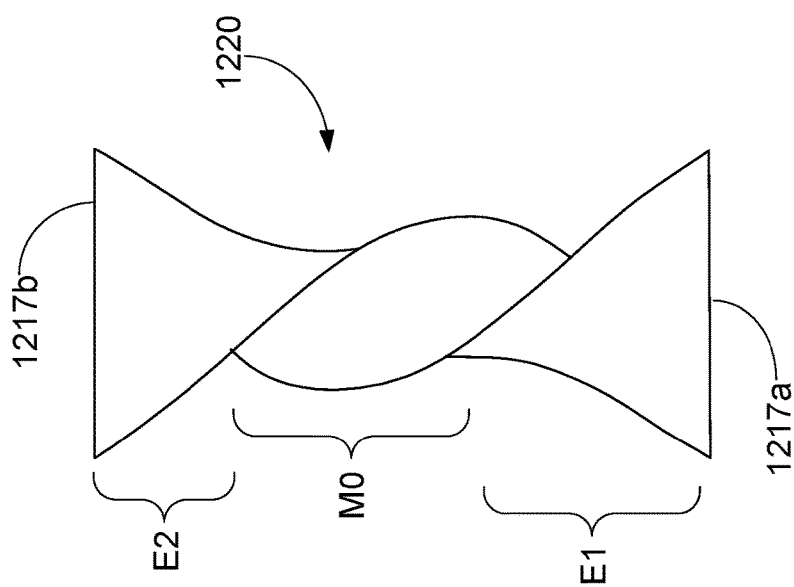
FIG. 12 is a simplified plan illustration of yet another alternate absorbent core according to the present invention

FIG. 12A illustrates yet another absorbent core 1220 in accordance with a further embodiment of the present invention. The inventive absorbent core 1220 features a narrow central region M0 and broader end regions E1, E2 and thus, provides yet another generally hourglass shaped absorbent core 1220. Notably, this configuration of an hourglass shaped core may be achieved with a single core element. In one of the simpler forms, the inventive absorbent core 1220 is formed by "twisting" a core element having the typical, generally rectangular, trapezoidal or parallelogram shape. More specifically, one end 1217a of the core element is turned or twisted clockwise (e.g., the bottom end 1217a in FIG. 12) and the other end 1217b is turned or "twisted" counter-clockwise. A twisted, narrow region of the core element is produced and provides the central region M0 of the absorbent core 1220. The wider, open ends of the twist are disposed as the end regions E1, E2 of the absorbent core 1220.

Figure 13A:
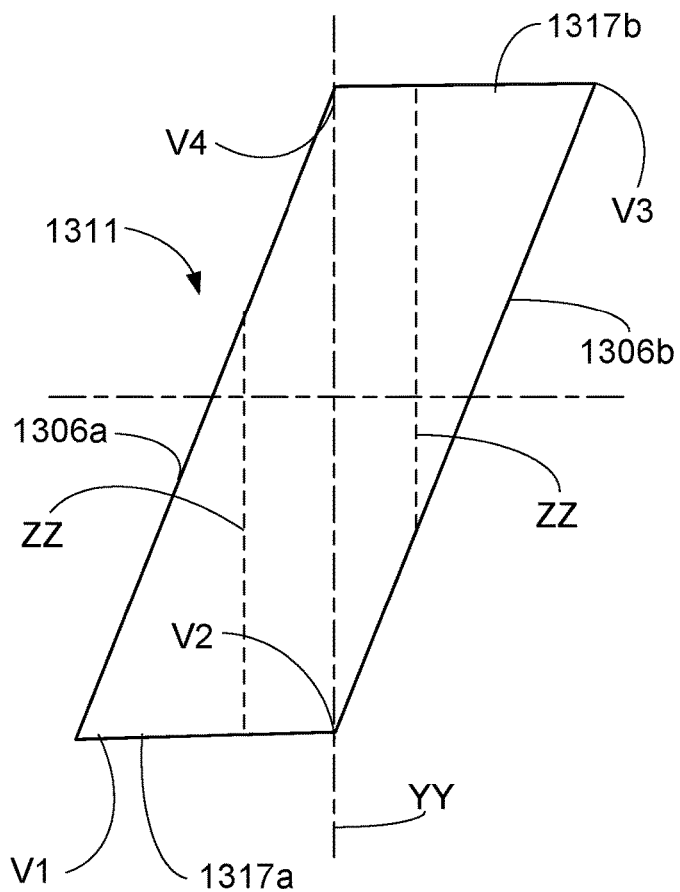
FIG. 13A is a simplified plan illustration of an absorbent core in FIG. 12, in a pre-applied state, according to the present invention.
Figure 13B:
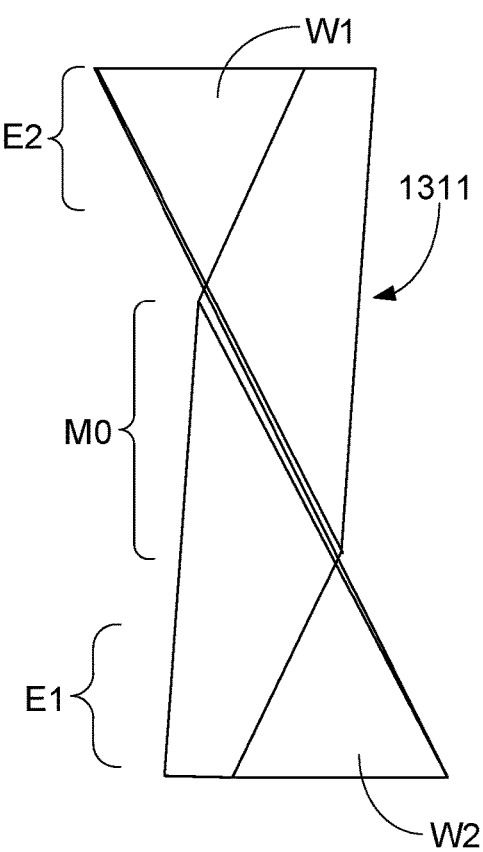
FIG. 13B is a simplified plan illustration of an absorbent core element according to yet another embodiment of the present invention.

FIGS. 13A-13B illustrates a method of making another "twisted" absorbent core 1310 or absorbent core element according to the present invention. Referring to FIG. 13A, an absorbent core element 1311 is first provided in a preferably generally parallelogram shape. The core element 1311 may be described as having a bottom end 1317a, a top end 1317b, a left side margin 1306a, a right side margin 1306b, and four corners V1, V2, V3, V4 each defined by the intersection of one of the ends 1317 and one of the side margins 1306. For purposes of this description, the core element 1311 is further described as having a pair of spaced apart twist axes ZZ and a longitudinal centerline YY preferably positioned generally parallel with and equidistantly between the twist axes ZZ. Each of twist axes ZZ is, therefore, laterally offset from the longitudinal centerline YY of the core element 1311. The twist axes ZZ are also preferably spaced laterally from opposing corners of the parallelogram shaped core element 1211.

As shown in FIG. 13A, the bottom left corner V1 is twisted in the counter clockwise direction about its twist axes ZZ while top right corner V3 is twisted in the clockwise direction about its twist axis ZZ. Referring to FIG. 13B, the resultant twisted absorbent core element 1311 has a somewhat distorted hourglass shape. Nevertheless, the resultant core element 1311 or resultant absorbent core construction provides certain features targeted by the invention. The absorbent core element 1311 has a narrow central region M0, wider end regions E1, E2, and a multi-layered primary absorbent region 1350 that imparts higher absorbency at specific target locations. The core element may be described further as having top and bottom V-shaped flaps W1, W2 (respectively) that extend laterally from the rest of the absorbent core element 1311.

Figure 13C:
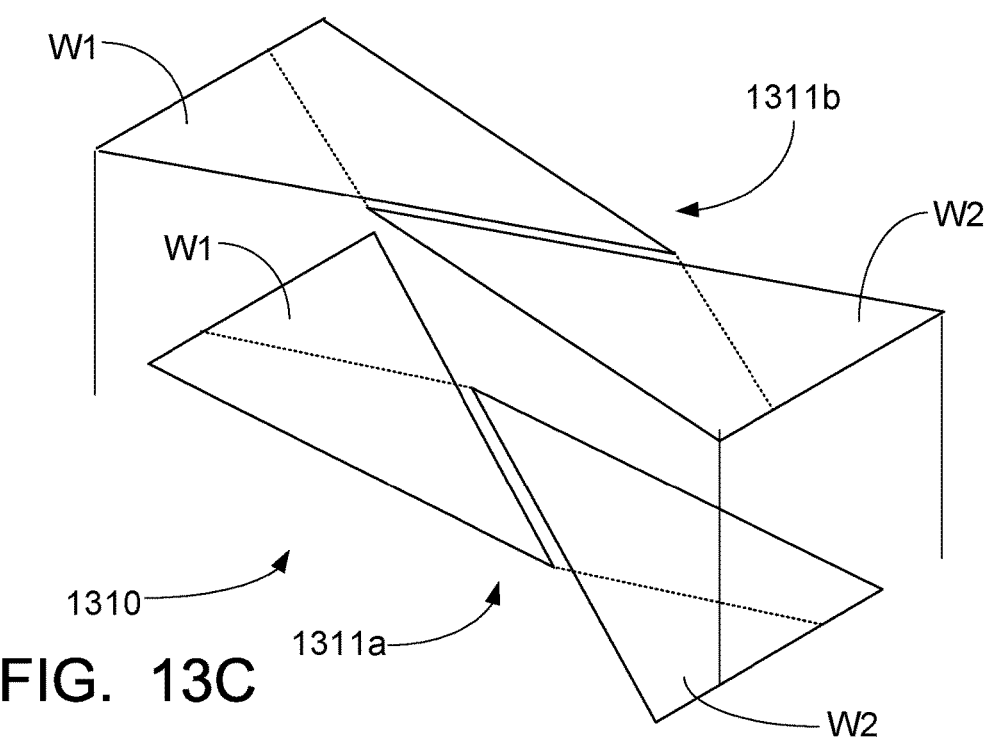
FIG. 13C is a perspective, exploded view of a dual layered absorbent core utilizing the absorbent core element in FIG. 13B, according to the present invention.
Figure 13D:
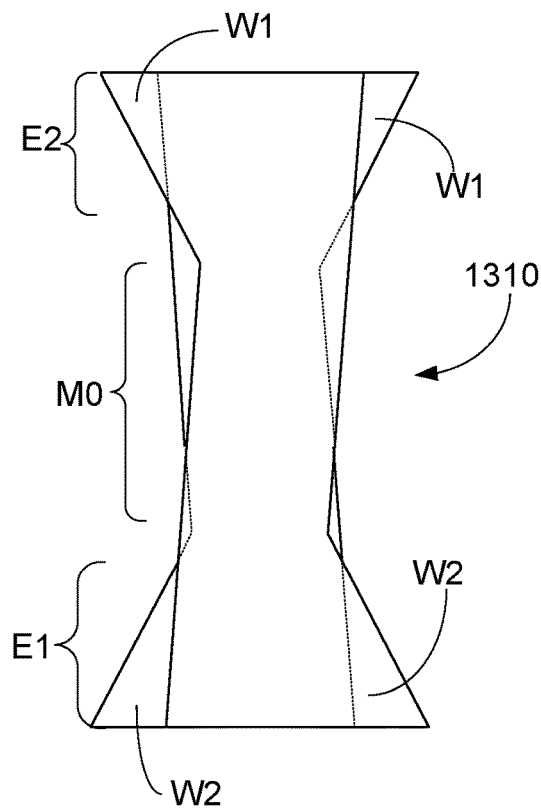
FIG. 13D is a plan illustration of the absorbent core in FIG. 13C.

Alternatively, the core element 1311 of FIG. 13B may be combined with another core element 1311 having substantially similar structure to produce an advanced embodiment of the present invention. FIGS. 13C and 13D illustrate the making of an improved absorbent core construction 1310 by combining two such absorbent core elements 1311. A top core element 1311b is positioned above a bottom core element 1311a, such that one is turned over relative to the other. Essentially, the core element 1311 in FIG. 13C is rotated 180° to the right and is presented as bottom core element 1311a in FIG. 13C. The flaps W1, W2 (of the core elements 1311) that are directly one atop the other extends, therefore, in opposite lateral directions, as shown in FIG. 13C. The first core element 1311b is then set upon (overlaid) the second core element 1311a. FIG. 13D depicts a resultant absorbent core 1310 that exhibits a more pronounced hourglass shape. The absorbent core also provides a more defined, and wider, top and bottom end regions E1, E2.

Figure 13F:
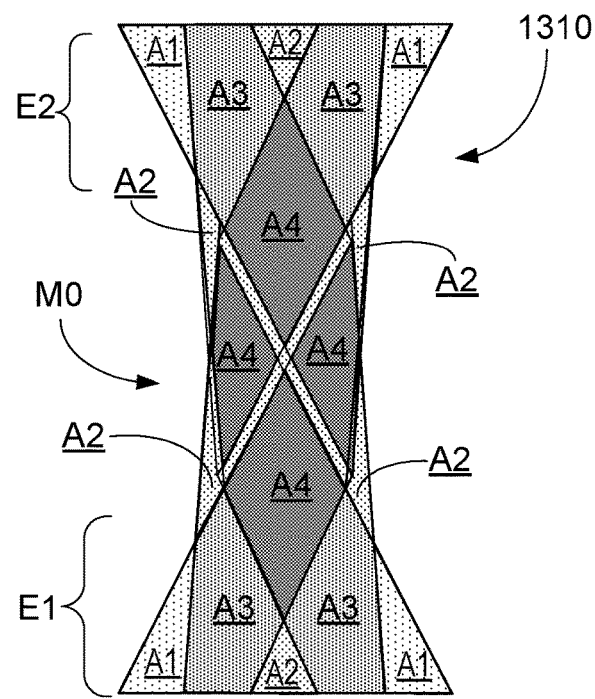
FIG. 13F is a plan illustration highlighting the varying absorbency in the absorbent core in FIG. 13E, according to the present invention.
Figure 13E:
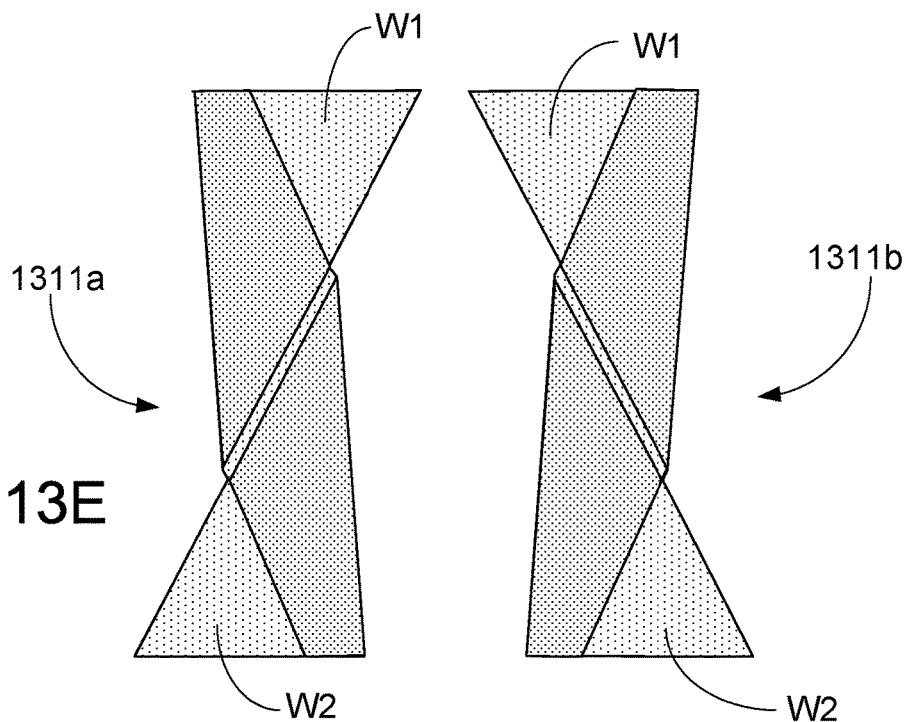
FIG. 13E is a plan illustration highlighting the varying absorbency in the pair of absorbent elements utilized in the absorbent core of FIG. 13D.

FIG. 13E illustrates the relative distribution of absorbent material in the core elements 13a, 13b utilized in the absorbent core 1310, prior to joining the two core elements 1311a, 1311b. The lighter areas represent regions provided by one layer of absorbent material while the darker areas represent regions with two layers of absorbent material, and thus, relatively higher absorbency. FIG. 13F illustrates the relative distribution of absorbent material in the resultant absorbent core 1310, which is comprised of the two core elements 1311a, 1311b. The illustration reflects an absorbent core 1310 with a multi-faceted absorbent profile along various directions (including along the longitudinal centerline). This resultant absorbent core 1310 features regions with single (A1), double (A2), triple (A3) and quadruple (A4) stacked layers of absorbent core material. The resultant absorbent profile reflects a highly absorbent region that is centered about the intersection of the longitudinal and lateral centerlines (YY, XX respectively), which provides the mid section M0. This highly absorbent region will correspond with, and provide sufficient coverage for, the crotch region of the absorbent article. The resultant absorbent core 1310 further provides broadened end regions E1, E2 that also feature varying absorbency, including broad regions extending from the mid section M0 with triple layers (A3) of absorbent material. One unique benefit of this multi-faceted design is the creation of channels with lesser amounts of absorbent material (fewer layers of core). For example, FIG. 13F shows an X-shaped channel C1 between the four regions A4. These channels C1 help to distribute fluid to other regions of the core 1310, thereby utilizing absorbent materials in other areas of the core 1310.

The resultant absorbent core 1310 provides certain targeted advantages and benefits. Firstly, the resultant absorbent core 1310 provides a better, more form fitting, fit for the wearer of the absorbent article as well as improved leakage prevention performance by providing absorbent material over a greater area of the article in the waist regions. Secondly the resultant absorbent structure provides a profiled, distribution of absorbent material throughout the article. A greater amount of absorbent material is provided in the crotch region of the article where receipt of fluids is expected. Concentrations of absorbent material, albeit lesser amounts, are also provided around the waist regions and side margins of the absorbent article. These absorbent regions perform an enhanced leak prevention function.

FIGS. 14A-14C provide a further embodiment of the present invention, featuring an enhanced absorbent core construction and absorbency profile. FIG. 14C depicts, more specifically, a dual layered core construction 1410. Initially, an absorbent element 1411a is presented having a generally rectangular configuration. The core element 1411a of this embodiment is provided with at least two laterally extending slits 1421 preferably positioned near or about the lateral centerline XX of the core element 1411a (and ultimately of the resultant absorbent core construction 1410). The laterally extending slits 1411 are directed inwardly from opposite side margins 1413 of the generally rectangular core element 1411a. In this embodiment, each of the lateral slits 1421 extends inwardly about $\frac{1}{5}^{th}$ the lateral width of the core element 1411a. Four imaginary folding lines 1422 are also presented in the generally rectangular core element 1411a. The folding lines 1422 also run inwardly from the side margins 1413 and downwardly toward the lateral centerline XX, thereby intersecting the end of the lateral slits 1421, as shown in FIG. 14A.

The imaginary folding lines 1422 may be created by a number of suitable means or methods, including initially pre-stressing the absorbent core element 1411a or stamping the absorbent core element 1411a prior to the folding steps. In a subprocess of making the absorbent core construction 1410, an urging force is applied to the side margins 1413 of the core element 1411a above and below the location of the lateral slits 1421. This force dislodges and/or urges a pair of resultant flaps 1423 inwardly about the imaginary folding lines 1422, as shown in FIG. 14B. The urging force may be provided by air jet mechanisms that blow or apply pressure on the side margins 1413 proximate the imaginary folding lines 1422. In alternative processes, a mechanical means, such as a piston, may be employed.

In any event, a pair of inwardly folding flaps 1423 is provided along each side margin 1413 above and below the former location of the lateral slit 1421. Turning to FIG. 14C, a second core element 1411b may be provided centrally atop the first core element 1411a, and underneath and inwardly from the four flaps 1423. The second core element 1411b may be applied on the first core element 1411a prior to the urging or folding steps (applied to the flaps 1423). Alternatively, the second core element 1411b may be inserted under the flaps 1423 after the folding operation. The second core element may also be applied over the top of the first or bottom core element and its folded side flaps, such that the folded flaps is placed between upper and lower core elements.

The result of either case is a generally hourglass-shaped absorbent core construction 1410, as shown by FIG. 14C. The absorbent core construction 1410 features an enhanced central absorbent region 1450, as provided by the second core element 1411b. The flaps 1423 also provide enhanced absorbency to the core construction 1410 (as the flaps 1423 are also made of highly absorbent material). Moreover, the absorbent flaps 1423 provide an enhanced absorbent region that functions as a leakage dam or sealant along the edges or side margins of the central region 1450. Additionally, as illustrated by FIG. 14C, the absorbent flaps 1423 help to secure the second core element 1411b centrally and atop the first core element 1411a. Specifically, the absorbent flaps 1423 wrap around the longitudinal edges of the second core element 1411b. In further embodiments, the second core element 1411b may be provided on top of the flaps 1423 of the first absorbent core element 1411a, or beneath the first core element 1411a. In either further embodiment, the second core element 1411b still provides enhanced absorbency in a central region 1450 of the hourglass-shaped absorbent core construction 1410.

Figure 15A:
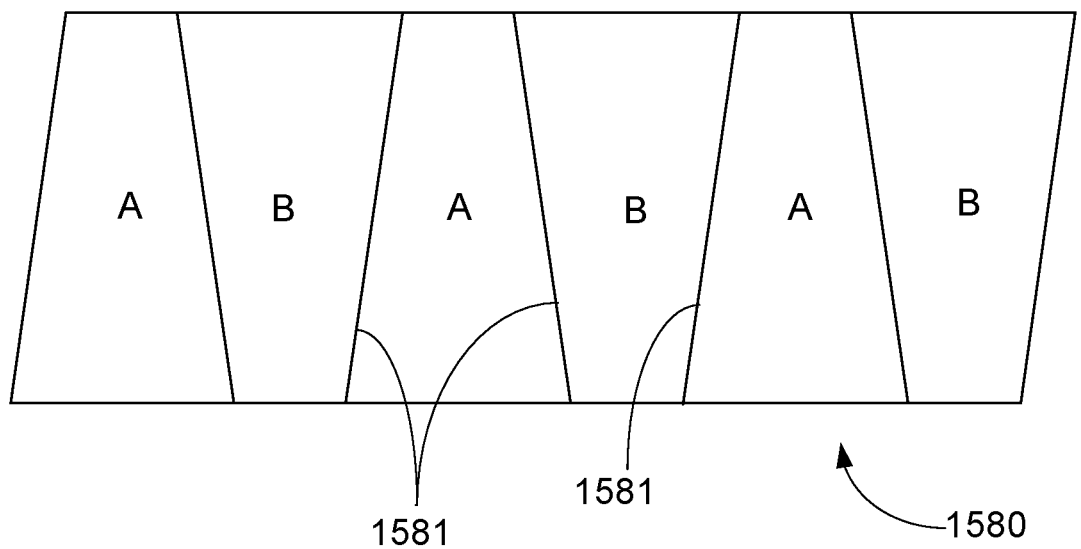
FIGS. 15A-15C are simplified illustrations of stages in the manufacture of a core construction from a web of core elements, according to the invention.
Figures 15B, 15C:
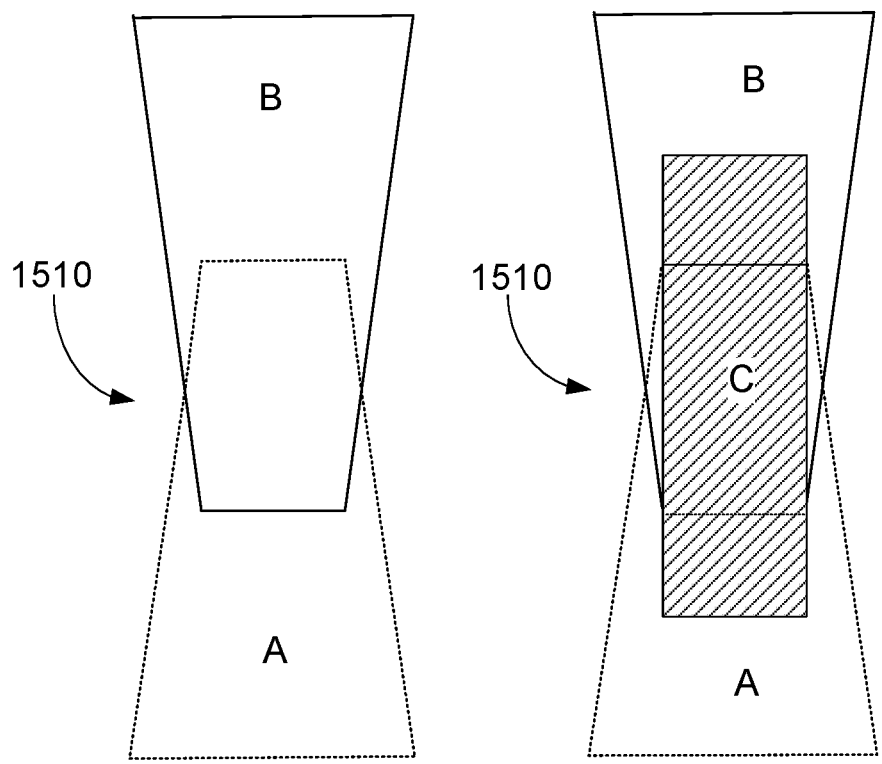

FIGS. 15A and 15B illustrate how a superimposed core construction 1510 such as that provided in FIG. 2A may be generated in an efficient and advantageous manner. As described previously, the core consists of two core elements A, B having a trapezoidal shape. The selection of a trapezoidal shape allows the core elements A, B to be derived from the same material source. Preferably, a web 1580 of core material, as shown in FIG. 15A, is presented as the core material source. Alternating trapezoidal core elements A and B are stamped on or cut from the web 1580. The two trapezoid shapes or blanks A, B are identical except that one is oriented 180 degrees from the other. Alternating inclined cuts 1581 may be made across the web 1580 (edge to edge) to produce and shape the two adjacent core elements A, B without waste of the web material. Each inclined cut 1581 is common to both blanks A, B and simultaneously defines a side of both trapezoid core elements A, B.

As shown in FIG. 15B, the two trapezoid blanks A, B are then overlaid to form the desired core construction. In further embodiments, a third core element C, which, in this case, has a rectangular shape, is disposed about the center of the core construction 1510 and overlays both trapezoid core elements A, B. The overlay of core elements A, B, C defines an even more highly absorbent central region.

It will be appreciated by those skilled in the art that other core elements shapes may be selected which allow adjacent blanks to be cut without waste material. The adjacent blanks will preferably be of an irregular shape (as required by various embodiments of the invention) and provided as mirror images of one another. With many irregular shapes, the blanks on the web will be oriented 180 degrees apart. In one application, instead of inclined sides or cuts, the cuts are curved and the core elements have curved outlines. In one particular embodiment, the core elements are preferably S-shaped and the blanks on the web may either be symmetrical along the longitudinal centerline or the blanks are oriented 180 degrees apart. Again, each cut or side is common to both blanks and defines corresponding sides of the adjacent blanks or core elements.

Figure 16A:
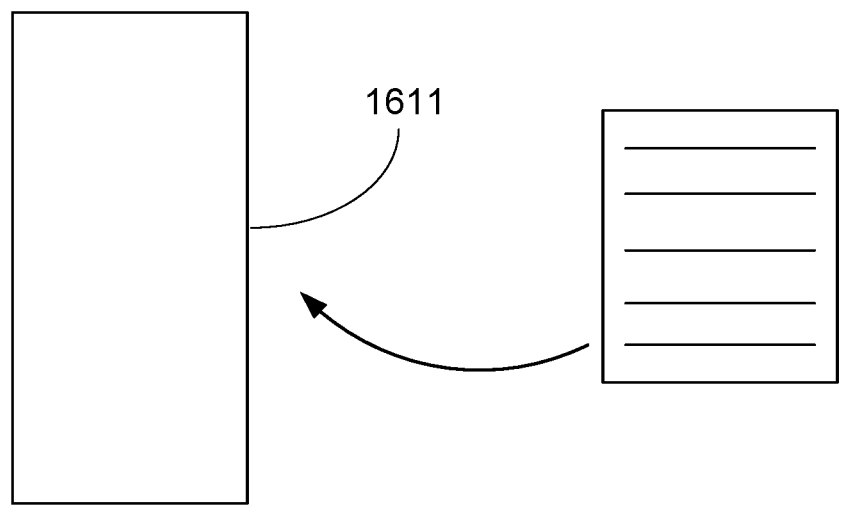
FIGS. 16A-16B are simplified illustrations of a method of laterally elasticize a core construction of the invention.
Figure 16B:
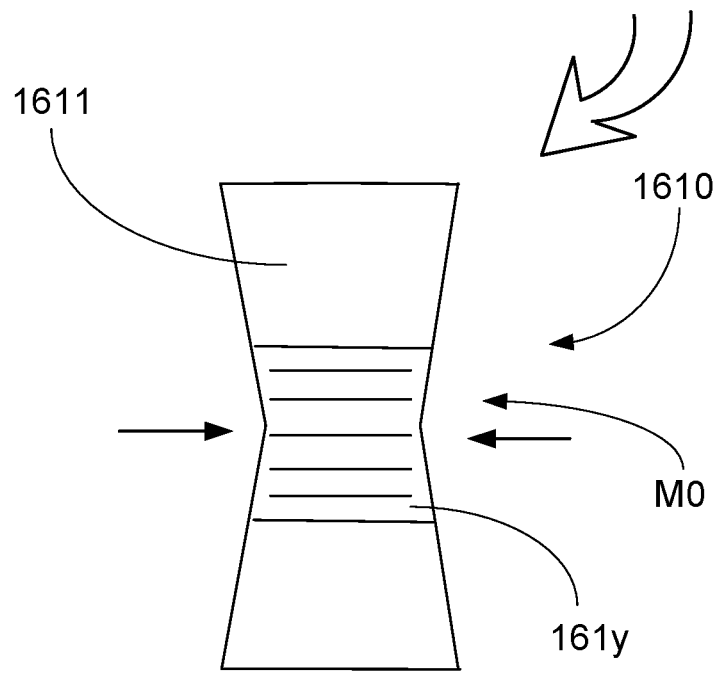

FIGS. 16A and 16B illustrate an exemplary method of laterally elasticizing a core construction 1610 similar to that of FIG. 6B. This particular method utilizes a rectangular, laterally elasticized composite 1619 such as that described in U.S. Pat. Nos. 7,361,246 and 7,462,172 (both of which are hereby incorporated by reference for all purposes, including being made a part of the present disclosure) (which patents have one or more inventors common to the present invention (s)). As described in these patent documents, the elastic composite 1619 may comprise at least one nonwoven sheet or other substrate and a plurality of lateral elastics thereon. In some embodiments, the elastic composite consists of elastics sandwiched between two nonwoven layers, but it is further contemplated that, for present purposes, only one substrate layer may be required. The elastic composite 1619 is applied, in tension, on a core element 1611 preferably centrally using suitable adhesives or the like. Once released form tension, the elastic composite 1619 contracts laterally, thereby also contracting the core element 1611 attached beneath the elastic composite 1619. This contraction creates a narrowed central region M0 of the resulting core construction 1610, as desired.

In respect to the embodiments of FIGS. 11A-11F, it is further contemplated that the longitudinally-directed elastics 1119 may be applied to the web 1180 of core element as one continuous strand. Sections of the continuous strand may be selectively severed to leave the intermittent series of elastics 1119 on the web 1180. Alternatively, the continuous strand may be adhered to the core material in the tensioned state (e.g., using glue or other suitable adhesive), then select portions of the continuous elastic strand are de-activated. Released from tension, the once-continuous elastic strand generates the intermittent series of contracted elastics 1119 and thus, the desired curved side margins (of the web 1180 and the resultant core elements 1111a, 1111b). In respect to the embodiments of FIGS. 11E and 11F, the slits 1133 may be made immediately after application of the continuous strand onto the web 1180.

The foregoing descriptions of various embodiments and aspects of the present invention have been presented for purposes of illustration and description. These descriptions are not intended to limit the invention to the various absorbent cores or articles, and processes disclosed. Various aspects of the invention are intended for applications other than diapers and training pants. The core constructions described may also be incorporated into or with other garments, textiles, fabrics, and the like, or combinations thereof. The core constructions described may also incorporate different components. These and other variations of the invention will become apparent to one generally skilled in the relevant consumer product art provided with the present disclosure. Consequently, variations and modifications commensurate with the above teachings, and the skill and knowledge of the relevant art, are within the scope of the present invention. The embodiments described and illustrated herein are further intended to explain the best modes for practicing the invention, and to enable others skilled in the art to utilize the invention and other embodiments and with various modifications required by the particular applications or uses of the present invention.

What is claimed is:

1. A disposable absorbent article comprising:
a central body defining a first waist end region including a first end edge, a second waist end region spaced longitudinally from the first waist end region and including a second end edge, and a crotch region positioned therebetween; and
an absorbent core situated between the end edges, the core including a plurality of elastics incorporated therewith such that the core is substantially laterally contracted in a narrowed region about the elastics; and
wherein the core includes a plurality of laterally aligned slits penetrating through a surface in the narrowed region and the slits provide voids in said narrowed region when contracted by the plurality of elastics; and the slits provide voids in said narrowed region; and
wherein said plurality of slits are arranged in longitudinally spaced apart rows, including a pair of rows longitudinally spaced apart from another and having a different number of said slits.

2. The article of claim 1, wherein the absorbent core includes at least one end region that is substantially non-elasticized, the at least one end region having a lateral width substantially wider than a lateral width of the narrowed region and wherein the absorbent core further includes a second end region spaced longitudinally from the at least one end region, the narrowed region being positioned longitudinally between the end regions and generally in the crotch region of the central body, and wherein the width of the narrowed region is generally reduced from a lateral width of the second end region; and
wherein said slits and said elastics are disposed centrally and in said narrowed region.

3. The disposable absorbent article of claim 2, wherein the absorbent core includes a first core element formed by materials imparting absorbent properties and a second core element formed by materials imparting absorbent properties, the second core element partially superimposing the first core element to form a multi-layer primary absorbent region of the absorbent core having an absorption capacity per unit area increased from an absorption capacity per unit area of other regions of the absorbent core; and
wherein the multi-layer absorbent region substantially coincides with the narrowed region; and wherein at least one of said first and second core elements is provided with said slits.

4. The article of claim 3, wherein the first or the second core elements includes and plurality of elastics incorporated therewith to form said narrowed region of the core, and wherein narrowed regions of the core elements are positioned adjacent one another to substantially form the narrowed region of the absorbent core.

5. The article of claim 3, wherein the plurality of elastics is attached to one of said core elements such that, in said narrowed region, said core elements are substantially contracted and said slits form said voids through one of said core elements.

6. The article of claim 3, wherein the second core element is shorter than the first core element and is at least partially superimposing the first core element to form the multi-layer primary absorbent region, narrowed regions of the core elements being situated to provide a substantially laterally contracted primary absorbent region.

7. The article of claim 6, wherein the second core element is disposed above the first core element and includes said slits that provide said voids penetrating through the second core element in the substantially laterally contracted primary absorbent region.

8. The article of claim 1, wherein the elastics are generally laterally aligned.

9. The article of claim 1, wherein the absorbent core further includes one core element placed adjacent a bottom core element with the plurality of elastics therebetween, the one core element being cut shorter than the bottom core element and the elastics being mutually spaced apart in the longitudinal direction and each directed in the lateral direction.

10. The disposable absorbent article of claim 1, wherein some of the rows have at least three laterally extending and laterally spaced apart slits and other rows have two or less laterally extending and laterally spaced apart slits.

11. The disposable absorbent article of claim 1, wherein at least one of said rows has one laterally extending slit and a plurality of the rows have two or more laterally extending and laterally spaced apart slits.

12. The disposable absorbent article of claim 1, wherein a plurality of the rows have more than two laterally extending and laterally spaced apart slits and a plurality of the rows have two or less laterally extending and laterally spaced apart slits.

13. The disposable absorbent garment of claim 1, wherein the core includes staggered rows of two and three of said slits.

14. The disposable absorbent garment of claim 1, wherein the core includes staggered rows of said slits, including rows of slits disposed between two other rows of slits wherein the row disposed in between the two rows has a lesser number of slits than each of the said two other rows.

15. A disposable absorbent article comprising:
a central body defining a first, waist end region including a first longitudinal end edge, a second waist end region spaced longitudinally from the first waist end region and including a second longitudinal end edge, and a crotch region positioned therebetween; and
an absorbent core situated between the end edges, the absorbent core including a first core element formed by materials imparting absorbent properties, and
a second core element formed by materials imparting absorbent properties;
wherein the second core element is disposed above the first core element and partially superimposes the first core element to form a multi-layer primary absorbent region of the absorbent core;
wherein the second core element has a plurality of slits penetrating therethrough, from an upper surface to said first core element, and one of the core elements includes a plurality of elastics attached thereto such that the core elements substantially contract in a narrowed central region coinciding with the crotch region and the slits provide voids through said second core element; and
wherein the slits and the elastics are located in the narrowed central region and are each generally directed in the lateral direction.

16. The article of claim 15, wherein the elastics are mutually spaced apart in the longitudinal direction.

17. The article of claim 16, wherein the slits are arranged in rows of one, two, or three mutually laterally spaced apart slits.

18. The disposable absorbent article of claim 15, wherein said slits are arranged in spaced apart rows, the rows including a pair of rows spaced apart from one another and having a different number of said slits.

19. The disposable absorbent article of claim 18, wherein at least one of the rows has at least three laterally spaced and laterally aligned slits, and at least one of the rows has two or less laterally aligned slits.

20. A disposable absorbent article comprising:
a central body defining a first waist end region including a first end edge, a second waist end region spaced longitudinally from the first waist end region and including a second end edge, and a crotch region positioned therebetween; and
an absorbent core situated between the end edges, the core including a plurality of elastics attached thereto such that the core is substantially laterally contracted in a narrowed region about the elastics; and
wherein the core further includes a core element having a plurality of slits penetrating therethrough such that the core element substantially contracts and the slits provide voids through said core element; and
wherein the elastic elements are selected from the group of elastic elements consisting of strands, elastic film, elastic adhesive, and elastic nonwovens, said core element having slits therein having a plurality of spaced apart rows of said slits, the slits in each row being spaced apart and generally directed in the lateral direction; and
wherein some of the rows have at least three laterally extending and laterally spaced apart slits and some rows have two or less laterally extending and laterally spaced apart slits.

21. The absorbent article of claim 20 wherein said core element with slits therein is placed above a bottom core element and is cut shorter than the bottom core element.

22. The disposable absorbent article of claim 21, wherein the absorbent core includes a first core element formed by materials imparting absorbent properties and a second core element formed by materials imparting absorbent properties, the second core element being bonded to the first core element and cut shorter than the first core element and partially superimposing the first core element to form a multi-layer primary absorbent region of the absorbent core; and
wherein the multi-layer absorbent region substantially coincides with the narrowed region; and wherein at least one of said first and second core elements is said core element with said slits therein; and
wherein an arrangement of said slits includes slits aligned and spaced apart in the lateral direction, and wherein the rows of said slits are mutually spaced apart in said longitudinal direction; and
wherein said elastics are pretensioned elastic elements attached to at least one of said core elements.

23. The absorbent article of claim 20, wherein an arrangement of said slits includes slits aligned and mutually spaced apart in the lateral direction, and a plurality of said slit arrangements are spaced apart in the longitudinal direction; and
wherein said elastics are pretensioned elastic elements attached to said core.

24. The absorbent article of claim 20, wherein the elastics are spaced apart in the longitudinal direction with a consistent pitch.

25. The absorbent article of claim 20, wherein the slits are generally directed in the lateral direction and staggered in rows of two and three slits.

26. The article of claim 20, wherein the slits are longitudinally spaced apart and provided in rows of one, two, and three slits.

27. The absorbent article of claim 20, wherein the slits have a length between 1-50 mm.

28. The absorbent article of claim 20, wherein the elastics are spaced apart longitudinally and each directed in the lateral direction, and wherein the elastics are disposed centrally relative to the core element wherein the length of the core element is longer than the arrangement of spaced apart elastics.

* * * * *